United States Patent
Rosenberg

(10) Patent No.: US 7,023,423 B2
(45) Date of Patent: Apr. 4, 2006

(54) LAPAROSCOPIC SIMULATION INTERFACE

(75) Inventor: Louis B. Rosenberg, Pleasanton, CA (US)

(73) Assignee: Immersion Corporation, San Jose, CA (US)

( * ) Notice: Subject to any disclaimer, the term of this patent is extended or adjusted under 35 U.S.C. 154(b) by 0 days.

(21) Appl. No.: 09/852,401

(22) Filed: May 9, 2001

(65) Prior Publication Data

US 2002/0018046 A1    Feb. 14, 2002

Related U.S. Application Data

(63) Continuation of application No. 08/870,956, filed on Jun. 6, 1997, now Pat. No. 6,246,390, which is a continuation of application No. 08/374,288, filed on Jan. 18, 1995, now Pat. No. 5,731,804.

(51) Int. Cl.
*G09G 5/08* (2006.01)
(52) U.S. Cl. ........................ 345/161; 345/156
(58) Field of Classification Search ............... 345/156, 345/157, 161, 162, 179; 24/471 XY; 434/45; 413/37, 38, 39; 715/701, 702
See application file for complete search history.

(56) References Cited

U.S. PATENT DOCUMENTS

| | | | |
|---|---|---|---|
| 2,906,179 A | 9/1959 | Bower | |
| 2,972,140 A | 2/1961 | Hirsch | |
| 3,157,853 A | 11/1964 | Hirsch | |
| 3,220,121 A | 11/1965 | Cutler | |
| 3,490,059 A | 1/1970 | Paulsen et al. | |
| 3,497,668 A | 2/1970 | Hirsch | |

(Continued)

FOREIGN PATENT DOCUMENTS

EP    0349086 A1    1/1990

(Continued)

OTHER PUBLICATIONS

Adelstein B. et al., "Design and Implementation of a Force Reflecting Manipulandum for Manual Control Research," 1992, pp. 1-24.

(Continued)

*Primary Examiner*—Chanh Nguyen
(74) *Attorney, Agent, or Firm*—Thelen Reid & Priest LLP; David B. Ritchie

(57) ABSTRACT

A method and apparatus for providing high bandwidth and low noise mechanical input and output for computer systems. A gimbal mechanism provides two revolute degrees of freedom to an object about two axes of rotation. A linear axis member is coupled to the gimbal mechanism at the intersection of the two axes of rotation. The linear axis member is capable of being translated along a third axis to provide a third degree of freedom. The user object is coupled to the linear axis member and is thus translatable along the third axis so that the object can be moved along all three degrees of freedom. Transducers associated with the provided degrees of freedom include sensors and actuators and provide an electromechanical interface between the object and a digital processing system. Capstan drive mechanisms transmit forces between the transducers and the object. The linear axis member can also be rotated about its lengthwise axis to provide a fourth degree of freedom, and, optionally, a floating gimbal mechanism is coupled to the linear axis member to provide fifth and sixth degrees of freedom to an object. Transducer sensors are associated with the fourth, fifth, and sixth degrees of freedom. The interface is well suited for simulations of medical procedures and simulations in which an object such as a stylus or a joystick is moved and manipulated by the user.

23 Claims, 10 Drawing Sheets

U.S. PATENT DOCUMENTS

| | | |
|---|---|---|
| 3,517,448 A | 6/1970 | Conyon et al. |
| 3,531,868 A | 10/1970 | Stevenson |
| 3,623,064 A | 11/1971 | Kagan |
| 3,775,865 A | 12/1973 | Rowan .......................... 35/17 |
| 3,795,150 A | 3/1974 | Eckhardt |
| 3,875,488 A | 4/1975 | Crocker et al. |
| 3,890,958 A | 6/1975 | Fister et al. |
| 3,902,687 A | 9/1975 | Hightower |
| 3,903,614 A | 9/1975 | Diamond et al. |
| 3,911,416 A | 10/1975 | Feder |
| 3,919,691 A | 11/1975 | Noll |
| 3,944,798 A | 3/1976 | Eaton |
| 4,127,752 A | 11/1978 | Lowthorp |
| 4,148,014 A | 4/1979 | Burson |
| 4,160,508 A | 7/1979 | Frosch et al. |
| 4,216,467 A | 8/1980 | Colston |
| 4,236,325 A | 12/1980 | Hall et al. |
| 4,262,549 A | 4/1981 | Schwellenbach |
| 4,333,070 A | 6/1982 | Barnes |
| 4,360,345 A | 11/1982 | Hon .......................... 434/262 |
| 4,391,282 A | 7/1983 | Ando et al. |
| 4,398,889 A | 8/1983 | Lam et al. |
| 4,436,188 A | 3/1984 | Jones |
| 4,448,083 A | 5/1984 | Hayashi |
| 4,464,117 A | 8/1984 | Foerst |
| 4,477,043 A | 10/1984 | Repperger |
| 4,477,973 A | 10/1984 | Davies |
| 4,484,191 A | 11/1984 | Vavra |
| 4,513,235 A | 4/1985 | Acklam et al. |
| 4,550,221 A | 10/1985 | Mabusth |
| 4,550,617 A | 11/1985 | Fraignier et al. |
| 4,571,834 A | 2/1986 | Fraser et al. |
| 4,581,491 A | 4/1986 | Boothroyd |
| 4,590,339 A * | 5/1986 | Scott-Jackson et al. ..... 200/6 A |
| 4,593,570 A | 6/1986 | Niskin |
| 4,599,070 A | 7/1986 | Hladky et al. |
| 4,601,206 A | 7/1986 | Watson |
| 4,604,016 A | 8/1986 | Joyce |
| 4,632,341 A | 12/1986 | Repperger et al. |
| 4,638,798 A | 1/1987 | Shelden et al. |
| 4,642,055 A | 2/1987 | Saliterman .................. 434/268 |
| 4,648,782 A | 3/1987 | Kraft |
| 4,653,011 A | 3/1987 | Iwano |
| 4,654,648 A | 3/1987 | Herrington et al. |
| 4,676,002 A | 6/1987 | Slocum |
| 4,679,331 A | 7/1987 | Koontz |
| 4,688,983 A | 8/1987 | Lindbom |
| 4,689,449 A | 8/1987 | Rosen |
| 4,703,443 A | 10/1987 | Moriyasu |
| 4,704,909 A | 11/1987 | Grahn et al. |
| 4,708,656 A | 11/1987 | De Vries et al. |
| 4,712,971 A | 12/1987 | Fyler |
| 4,713,007 A | 12/1987 | Alban |
| 4,750,487 A | 6/1988 | Zanetti |
| 4,769,763 A | 9/1988 | Trieb et al. |
| 4,775,289 A | 10/1988 | Kazerooni |
| 4,782,327 A | 11/1988 | Kley et al. |
| 4,787,051 A | 11/1988 | Olson |
| 4,791,934 A | 12/1988 | Brunnett |
| 4,794,392 A | 12/1988 | Selinko |
| 4,798,919 A | 1/1989 | Miessler et al. |
| 4,800,721 A | 1/1989 | Cemenska et al. |
| 4,803,413 A | 2/1989 | Kendig et al. |
| 4,811,608 A | 3/1989 | Hilton |
| 4,819,195 A | 4/1989 | Bell et al. |
| 4,839,838 A | 6/1989 | LaBiche et al. |
| 4,849,692 A | 7/1989 | Blood |
| 4,861,269 A | 8/1989 | Meenen, Jr. |
| 4,878,374 A | 11/1989 | Nelson |
| 4,879,556 A | 11/1989 | Duimel |
| 4,879,668 A | 11/1989 | Cline et al. .................. 364/522 |
| 4,885,565 A | 12/1989 | Embach |
| 4,888,877 A | 12/1989 | Enderle et al. |
| 4,891,764 A | 1/1990 | McIntosh |
| 4,891,889 A | 1/1990 | Tomelleri |
| 4,907,970 A | 3/1990 | Meenen, Jr. |
| 4,907,973 A | 3/1990 | Hon |
| 4,930,770 A | 6/1990 | Baker |
| 4,934,694 A | 6/1990 | McIntosh |
| 4,942,545 A | 7/1990 | Sapia |
| 4,945,305 A | 7/1990 | Blood |
| 4,945,501 A | 7/1990 | Bell et al. |
| 4,949,119 A | 8/1990 | Moncrief et al. |
| 4,961,138 A | 10/1990 | Gorniak |
| 4,961,267 A | 10/1990 | Herzog |
| 4,962,448 A | 10/1990 | DeMaio et al. |
| 4,962,591 A | 10/1990 | Zeller et al. |
| 4,982,504 A | 1/1991 | Söderberg et al. |
| 4,982,618 A | 1/1991 | Culver |
| 4,983,786 A | 1/1991 | Stevens et al. |
| 5,007,085 A | 4/1991 | Greanias et al. |
| 5,007,300 A | 4/1991 | Siva |
| 5,019,761 A | 5/1991 | Kraft |
| 5,022,384 A | 6/1991 | Freels |
| 5,022,407 A | 6/1991 | Horch et al. |
| 5,035,242 A | 7/1991 | Franklin et al. |
| 5,038,089 A | 8/1991 | Szakaly |
| 5,040,306 A | 8/1991 | McMurtry et al. |
| 5,044,956 A | 9/1991 | Behensky et al. |
| 5,050,608 A | 9/1991 | Watanabe et al. |
| 5,072,361 A | 12/1991 | Davis et al. |
| 5,078,152 A | 1/1992 | Bond et al. |
| 5,088,046 A | 2/1992 | McMurtry |
| 5,088,055 A | 2/1992 | Oyama |
| 5,095,303 A | 3/1992 | Clark et al. |
| 5,103,404 A | 4/1992 | McIntosh |
| 5,107,080 A * | 4/1992 | Rosen .......................... 200/6 A |
| 5,107,719 A | 4/1992 | Kota |
| 5,116,051 A | 5/1992 | Moncrief et al. |
| 5,116,180 A | 5/1992 | Fung et al. |
| 5,126,948 A | 6/1992 | Mitchell et al. |
| 5,128,671 A | 7/1992 | Thomas, Jr. |
| 5,131,844 A | 7/1992 | Marinaccio et al. |
| 5,132,672 A | 7/1992 | Clark |
| 5,139,261 A | 8/1992 | Openiano |
| 5,142,506 A | 8/1992 | Edwards |
| 5,142,931 A | 9/1992 | Menahem |
| 5,143,505 A | 9/1992 | Burdea et al. |
| 5,146,566 A | 9/1992 | Hollis et al. |
| 5,148,377 A | 9/1992 | McDonald |
| 5,149,270 A | 9/1992 | McKeown .................. 434/262 |
| 5,156,363 A | 10/1992 | Cizewski et al. |
| 5,165,897 A | 11/1992 | Johnson |
| 5,175,459 A | 12/1992 | Danial et al. |
| 5,178,012 A | 1/1993 | Culp |
| 5,181,181 A | 1/1993 | Glynn |
| 5,182,557 A | 1/1993 | Lang |
| 5,184,306 A | 2/1993 | Erdman et al. |
| 5,184,319 A | 2/1993 | Kramer |
| 5,185,561 A | 2/1993 | Good et al. |
| 5,186,695 A | 2/1993 | Mangseth et al. |
| 5,187,874 A | 2/1993 | Takahashi et al. |
| 5,189,806 A | 3/1993 | McMurtry et al. |
| 5,193,963 A | 3/1993 | McAffee et al. |
| 5,197,003 A | 3/1993 | Moncrief et al. |
| 5,204,824 A | 4/1993 | Fujimaki |
| 5,209,131 A | 5/1993 | Baxter |
| 5,209,661 A | 5/1993 | Hidreth et al. |
| 5,212,473 A | 5/1993 | Louis |
| 5,220,260 A | 6/1993 | Schuler |
| 5,223,776 A | 6/1993 | Radke et al. |
| 5,228,356 A | 7/1993 | Chuang |
| 5,230,623 A | 7/1993 | Guthrie et al. |
| 5,240,417 A | 8/1993 | Smithson et al. |

| | | |
|---|---|---|
| 5,243,266 A | 9/1993 | Kasagami et al. |
| 5,251,127 A | 10/1993 | Raab |
| 5,251,156 A | 10/1993 | Heier et al. |
| 5,259,120 A | 11/1993 | Chapman et al. |
| 5,259,894 A | 11/1993 | Sampson |
| 5,262,777 A | 11/1993 | Low et al. |
| 5,264,768 A | 11/1993 | Gregory et al. |
| 5,265,630 A | 11/1993 | Hartmann |
| 5,271,290 A | 12/1993 | Fischer |
| 5,275,174 A | 1/1994 | Cook |
| 5,275,565 A | 1/1994 | Moncrief |
| 5,283,970 A | 2/1994 | Aigner |
| 5,289,273 A | 2/1994 | Lang |
| 5,295,694 A | 3/1994 | Levin ............ 273/447 |
| 5,296,846 A | 3/1994 | Ledley |
| 5,297,057 A | 3/1994 | Kramer et al. |
| 5,299,810 A | 4/1994 | Pierce et al. |
| 5,309,140 A | 5/1994 | Everett, Jr. et al. |
| 5,327,790 A | 7/1994 | Levin et al. |
| 5,334,027 A | 8/1994 | Wherlock |
| 5,351,692 A | 10/1994 | Dow et al. |
| 5,354,162 A | 10/1994 | Burdea et al. |
| 5,379,663 A | 1/1995 | Hara |
| 5,384,460 A | 1/1995 | Tseng |
| 5,389,865 A | 2/1995 | Jacobus et al. |
| 5,396,266 A | 3/1995 | Brimhall |
| 5,397,323 A | 3/1995 | Taylor et al. |
| 5,402,582 A | 4/1995 | Raab |
| 5,403,191 A | 4/1995 | Tuason ............ 434/262 |
| 5,405,152 A | 4/1995 | Katanics et al. |
| 5,412,880 A | 5/1995 | Raab |
| 5,414,337 A | 5/1995 | Schuler |
| 5,417,696 A | 5/1995 | Kashuba et al. |
| 5,429,140 A | 7/1995 | Burdea et al. |
| 5,436,542 A | 7/1995 | Petelin et al. |
| 5,436,622 A | 7/1995 | Gutman et al. |
| 5,436,640 A | 7/1995 | Reeves |
| 5,437,607 A | 8/1995 | Taylor |
| 5,445,166 A | 8/1995 | Taylor |
| 5,459,382 A | 10/1995 | Jacobus et al. |
| 5,466,213 A | 11/1995 | Hogan et al. |
| 5,467,763 A | 11/1995 | McMahon et al. |
| 5,473,235 A | 12/1995 | Lance et al. |
| 5,491,477 A | 2/1996 | Clark et al. |
| 5,512,919 A | 4/1996 | Araki |
| 5,513,100 A | 4/1996 | Parker et al. |
| 5,547,382 A | 8/1996 | Yamasaki et al. |
| 5,547,383 A | 8/1996 | Yamaguchi |
| 5,575,761 A | 11/1996 | Hajianpour |
| 5,576,727 A | 11/1996 | Rosenberg et al. |
| 5,587,937 A | 12/1996 | Massie et al. |
| 5,589,828 A | 12/1996 | Armstrong |
| 5,589,854 A | 12/1996 | Tsai |
| 5,591,924 A | 1/1997 | Hilton |
| 5,609,485 A | 3/1997 | Bergman et al. ............ 434/262 |
| 5,623,582 A | 4/1997 | Rosenberg |
| 5,625,576 A * | 4/1997 | Massie et al. ............ 703/6 |
| 5,629,594 A | 5/1997 | Jacobus et al. |
| 5,642,469 A | 6/1997 | Hannaford et al. |
| 5,643,087 A | 7/1997 | Marcus et al. |
| 5,666,138 A | 9/1997 | Culver |
| 5,690,582 A | 11/1997 | Ulrich et al. |
| 5,704,791 A | 1/1998 | Gillio ............ 434/262 |
| 5,709,219 A | 1/1998 | Chen et al. |
| 5,742,278 A | 4/1998 | Chen et al. |
| 5,766,016 A | 6/1998 | Sinclair et al. |
| 5,767,839 A | 6/1998 | Rosenberg |
| 5,769,640 A * | 6/1998 | Jacobus et al. ............ 434/262 |
| 5,800,179 A | 9/1998 | Bailey |
| 5,808,665 A | 9/1998 | Green |
| 5,821,920 A | 10/1998 | Rosenberg et al. |
| 5,920,319 A | 7/1999 | Vining et al. ............ 345/420 |
| 6,024,576 A | 2/2000 | Bevirt et al. |
| 6,037,927 A | 3/2000 | Rosenberg |
| 6,104,382 A | 8/2000 | Martin et al. |
| 6,111,577 A | 8/2000 | Zilles et al. |
| 6,154,198 A | 11/2000 | Rosenberg |
| 6,160,489 A | 12/2000 | Perry et al. |
| 6,215,470 B1 | 4/2001 | Rosenberg et al. |
| 6,246,390 B1 | 6/2001 | Rosenberg |
| RE37,528 E | 1/2002 | Hannaford et al. |
| 6,422,941 B1 | 7/2002 | Thorner et al. |

FOREIGN PATENT DOCUMENTS

| | | |
|---|---|---|
| EP | 0391376 | 10/1990 |
| FR | 8519304 | 12/1995 |
| GB | 2187101 | 9/1987 |
| GB | 225411 | 10/1992 |
| JP | 4-34610 | 5/1990 |
| JP | H2-185278 | 7/1990 |
| JP | H4-8381 | 1/1992 |
| JP | H5-192449 | 8/1993 |
| JP | H7-24147 | 1/1995 |
| WO | WO91/06935 | 5/1991 |
| WO | WO92/16141 | 10/1992 |
| WO | WO94/00052 | 1/1994 |
| WO | WO9426167 | 11/1994 |
| WO | WO9510080 | 4/1995 |
| WO | WO9520787 | 8/1995 |
| WO | WO9520788 | 8/1995 |
| WO | WO9520877 | 8/1995 |
| WO | WO9532459 | 11/1995 |
| WO | WO9616397 | 5/1996 |
| WO | WO9622591 | 7/1996 |
| WO | WO96/39944 | 12/1996 |
| WO | WO01/11775 A1 | 2/2001 |

OTHER PUBLICATIONS

Buttolo, P. et al., "Pen-Based Force Display for Precision Manipulation in Virtual Environments," IEEE 0-8186-7084, 1995, pp. 217-224.

Ramstein, C. et al., "The Pantograph: A Large Workspace Haptic Device for a Multimodal Human-Computer Interaction," Computer-Human Interaction, CHI '94, 1994, pp. 1-3.

Payette, J. et al., "Evaluation of a Force Feedback (Haptic) Computer Pointing Device in Zero Gravity," DSC-vol. 58, Proceedings of the ASME Dynamics Systems and Control Division, ASME 1996, pp. 547-553.

Ramstein, Christophe, "Combining Haptic and Braille Technologies: Design Issues and Pilot Study," ASSETS '96, 2nd Annual ACM Conf. on Assistive Technologies: Design Issues and Pilot Study, 1996, pp. 37-44.

Hayward, V. et al., "Design and Multi-Objective Optimization of a Linkage for a Haptic Interface," *Advances in Robot Kinematics and Computationed Geometry*, Kluwer Academic Publishers, 1994, pp. 359-368.

Millman, P. et al., "Design of a Four Degree-of-Freedom Force-Reflecting Manipulandum with a Specified Force/Torque Workspace," Proceedings of the 1991 IEEE Int'l Conf. on Robotics an Automation, 1991, pp. 1488-1493.

Tavkhelidze, D.S. et al., "Kinematic Analysis of Five-Link Spherical Mechanisms," *Mechanism and Machine Theory*, vol. 9, 1974, pp. 181-190.

Hirota, K. et al., "Development of Surface Display," IEEE 0-7803-1363, 1993, pp. 256-262.

Brooks, F. et al., "Project GROPE-Haptic Displays for Scientific Visualization," Computer Graphics, vol. 24, No. 4, 1990, pp. 177-185.

Iwata, Hiroo, "Artificial Reality with Force-feedback: Development of Desktop Virtual Space with Compact Master Manipulator," Computer Graphics, vol. 24, No. 4, 1990, pp. 165-170.

Iwata, H. et al., "Volume Haptization," IEEE 0-8186-4910-0/93, 1993, pp. 16-18.

Iwata, Hiroo, "Pen-based Haptic Virtual Environment," IEEE 0-7803-1363-1/93, 1993, pp. 287-292.

Snow, E. et al., "Compact Force-Reflecting Hand Controller," NASA Contract No. NAS 7-918, 1991.

McAffee, D. et al., "Teleoperator Subsystem / Telerobot Demonstrator: Force Reflecting Hand Controller Equipment Manual," JPL D-5172, 1988.

Schmult, B. et al., "Application Areas for a Force-feedback Joystick," DSC-vol. 49, Advances in Robotics, Mechatronics, and Haptic Interfaces, ASME 1993, pp. 47-54.

Howe, R., "Task Performance with a Dextrous Teleoperated Hand System," Proceedings of SPIE, vol. 1833, 1992, pp. 1-9.

Rosenberg, L. et al., "Perceptual Decomposition of Virtual Haptic Surfaces," Proc. IEEE Symp. on Research Frontiers in Virtual Reality, 1993.

Rosenberg, L., "Virtual Haptic Overlays Enhance Performance in Telepresence Tasks," Stanford Univ., Dept. of Mech. Engineering, 1994.

Rosenberg, L., "Virtual Fixtures as Tools to Enhance Operator Performance in Telepresence Environments," SPIE Telemanipulator Technology, 1993.

Ellis, R. E. et al., "Design and Evaluation of a High-Performance Prototype Planar Haptic Interface," DSC-vol. 49, Advances in Robotics, Mechatronics, and Haptic Interfaces, ASME 1993.

Bejczy, A. et al., "The Phantom Robot: Predictive Displays for Teleoperation with Time Delay," IEEE CH2876-1/90, 1990.

Colgate, J. et al., "Implementation of Stiff Virtual Walls in Force-Reflecting Interfaces," Dept. of Mech. Engineering, Northwestern Univ., 1993.

Hannaford, B. et al., "Performance Evaluation of a Six-Axis Generalized Force-Reflecting Teleoperator," IEEE Transactions on Systems, Man, and Cybernetics, vol. 21, No. 3, 1991.

Fischer, P., "Specification and Design of Input Devices for Teleoperation," IEEE CH2876-1/90, 1990.

Atkinson, W. et al., "Computing with Feeling," Comput. & Graphics, vol. 2.

Rosenberg, L., "The Use of Virtual Fixtures to Enhance Operator Performance in Time Delayed Teleoperation," Armstrong Laboratory, Crew Systems Directorate, Air Force Materiel Command, 1993.

Rosenberg, L., "Perceptual Design of a Virtual Rigid Surface Contact," Armstrong Laboratory, Crew Systems Directorate, Air Force Materiel Command, 1993.

Russo, M., "The Design and Implementation of a Three Degree-of-freedom Force Output Joystick," Dept. of Mech. Engineering, 1990.

Adelstein B. et al., "A High Performance Two Degree-of-Freedom Kinesthetic Interface,"Massachusetts Institute of Technology, 1992.

Batter, J. et al., "Grope-1: A Computer Display to the Sense of Feel," Proc. IFIP Congress, 1971.

Minsky, M. et al., "Feeling and Seeing: Issues in Force Display," ACM 089791-351-5, 1990.

Ouh-young, M. et al., "Force Display Performs Better than Visual Display in a Simple 6-D Docking Task," 1989 IEEE Int'l Conf. on Robotics and Automation, IEEE CH2750-8, 1989.

Jacobsen, S.C., "High-Performance, High Dexterity, Force Reflective Teleoperator II," ANS Topical Meeting on Robotics and Remote Systems, 1991.

Kilpatrick, Paul, "The Use of Kinesthetic Supplement in an Interactive Graphics System," Univ. of North Carolina at Chapel Hill, 1976.

Herndon, J. N., "The State-of-the-Art Model M-2 Maintenance System," Proc. of 1984 Nat'l Topical Meeting on Robotics and Remote Handling in Hostile Environments, ANS, 1984.

Ouh-young, M., "Force Display in Molecular Docking," Univ. of North Carolina at Chapel Hill, 1990.

Ouh-young, Ming et al., "Using a Manipulator for Force Display in Molecular Docking," IEEE 1988, pp. 1824-1829.

Gotow, J.K., et al., "Perception of Mechanical Properties at the Man-Machine Interface," IEEE 1987, pp. 688-689.

"Proceedings of the IFIP Congress 65," International Federation for Information Processing, Information Processing 1965, vol. 3, New York, May 24-29, 1965, pp. 506.

Noll, A. Michael, "Man-Machine Tactile Communication Dissertation," Polytechnic Institute of Brooklyn, Jun. 1971, pp. 1-88.

Burdea, Grigore et al., "Dextrous Telerobotics with Force Feedback—An Overview," Robotica 1991, vol. 9.

Yamakita, M. et al., "Tele-Virtual Reality of Dynamic Mechanical Model," IEEE Jul. 7-10, 1992, pp. 1103-1110.

Kim, Won S. et al., "Graphics Displays for Operator Aid in Telemanipulation," IEEE 1991, pp. 1059-1067.

Kim, Won S. et al, "A Teleoperation Training Simulator with Visual and Kinesthetic Force Virtual Reality", Human Vision, Visual Proceedings, Proc. SPIE 1666, San Jose, CA, Feb. 1992.

"High Performance Model of the Immersion Probe," Immersion Probe-MD.TM., Immersion Corporation.

"Curso Waldo," Designer's Corner-Useful Technology for Your Idea File Design News, Mar. 7, 1994, pp. 63.

The Personal Digitizer, Immersion Corporation, 1994.

Immersion Probe.TM., 3D Human Interface Tool, Immersion Corporation, 1994.

Kotoku, Tetsuo et al., "Environment Modeling for the Interactive Display (EMID) Used in Telerobotic Systems," IEEE Nov. 3-5, 1991, pp. 99-1004.

Tan, Hong Z. et al., "Human Factors for the Design of Force-Reflecting Haptic Interfaces," Tan, Srinivasan , Eberman, & Chang, ASME WAM 1994, pp. 1-11.

Burdea, Grigore et al., "Distributed Virtual Force Feedback," IEEE, May 2, 1993, pp. 25-44.

Kim. Won S. et al., "A Teleoperation Training Simulator with Visual and Kinesthetic Force Virtual Reality".

"Useful Technology for Your Idea File," Design News, Mar. 7, 1994, p. 63.

"3D Human Interface Tool," Immersion Probe.TM., Immersion Human Interface Corporation 1994.

Krueger, Myron W., "Artificial Reality" 1988, pp. 54-75.

Wiker, Steve F. et al., "Development of Tactile Mice for Blind Access to Computers: Importance of Stimulation Locus, Object Size, and Vibrotactile Display Resolution," Proceedings of the Human Factors Society 35th Annual Meeting 1991, pp. 708-712.

Smith, Geoffrey, "Call it Palpable Progress," Business Week, Oct. 9, 1995, pp. 95-96.

Fisher, S.S. et al., "Virtual Environment Display System," ACM 1986 Workshop on Interactive 3D Graphics, Oct. 1986.

Merril, J. et al., "Cyber Surgery: Cutting Costs, Sewing Benefits," Virtual Reality Special Report, 1994, pp. 39, 40, 42.

Cover, S. et al., "Interactively Deformable Models for Surgery Simulation," IEEE Computer Graphics & Applications, 1993, pp. 68-75.

Merril, J. et al., "Virtual Reality for Trade Shows and Individual Physician Training," Medical Applications, 1994, pp. 40-44.

Merril, J. et al., "Surgical Simulation Using Virtual Reality Technology: Design, Implementation, and Implications," Surgical Technology International III, pp. 53-60.

Hon, D., "Ixion's Realistic Medical Simulations," Virtual Reality World, 1994, pp. 58-62.

Cover, S. et al., "Interactively Deformable Models for Surgery Simulation," IEEE Computer Graphics and Applications, 1993, pp. 68-75.

Mazier, B. et al., "Computer Assisted Interventionist Imaging: Application to the Vertebral Column Surgery," Annual Int'l Conf. of IEEE Engineering in Medicine and Biology Society, vol. 12, No. 1, 1990, pp. 430-431.

Bostrom, M. et al., "Design of an Interactive Lumbar Puncture Simulator with Tactile Feedback," IEEE 0-7803-1363-1, 1993, pp. 280-286.

Stone, R. et al., "Virtual Environment Training Systems for Laparoscopic Surgery," The Journal of Medicine and Virtual Reality, pp 42-51.

Zan et al., "Manual resolution of Compliance When Work and Force Cues are Minimized," DSC—vol. 49, Advances In Robotics, Mechatronics and Haptic Interfaces ASME 1993, The American Society og Mechanical Engineers, pp. 99-104, (Nov. 28-Dec. 3, 1993).

Adelstein et al., Human Machine Interfaces for Teleoperators and Virtual Environments, NASA Conference Publication 10071, N95-14042, pp. 108-113, (Mar. 4-Sep. 1990).

Adelstein et al., "Design and Implementation of a Force Reflecting Manipulendum for Manual Control research," DSC-vol. 42, Advances in Robotics, pp. 1-12, (1992).

Baigrie, "Electric Control Loading—A Low Cost, High Performance Alternative," Proceedings, pp. 247-264, (Nov. 6-8, 1990).

Iwata, "Pen-based Haptic Virtual Environment," 0-7805-1383-1/93 IEEE, pp 287-292, (1993).

Iwata et al., "Volume Haptization," 0-8186-4910-0/93 IEEE, pp. 16-23, (1993).

Iwata, "Artificial Reality with Force-feedback: Development of Desktop Virtual Space with Compact Master Manipulator," Computer Graphics, vol. 24, No. 4—ACM-0-89791-344-2/90/008/0165, pp. 165-170, (Aug. 1990).

Russo, "The Design and Implementation of a Three Degree of Freedom Force Output Joystick," MIT Libraries Archives Aug. 14, 1990, pp. 1-131, (May 1990).

Burdea et al., "Dextrous telerobotics with force feedback—an overview, Part 2; Human factors," Robotics (1991) vol. 9, pp. 291-298, (Jun. 22, 1990).

Brooks et al., "Hand Controllers for Teleoperation—A State-of-the-Art Technology Survey and Evaluation," JPL Publication 85-11; NASA-CR-175890; N85-28559, pp. 1-84, (Mar. 1, 1985).

Jones et al., "A perceptual analysis of stiffness," ISSN 0014-4819 Springer International (Springer-Verlag); Experimental Brain Research, vol. 79, No. 1, pp. 150-156, (1990).

Burdea et al., "Distributed Virtual Force Feedback, Lecture Notes for Workshop on Force Display in Virtual Environments and its Application to Robotic Teleoperation," 1993 IEEE International Conference on Robotics and Automation, pp. 25-44, (May 2, 1993).

Snow et al., "Compact Force-Reflecting Hand Controller," NASA TechBriefs, Apr., 1991, vol. 5, No. 4, p. 88, (Apr. 1991).

Snow et al., "Model-X Force-Reflecting-Hand-Controller," NT Control No. MPO-17851; JPL Case No. 5348, pp. 1-4, (Jun. 15, 1989).

Bejczy et al., "Controlling Remote Manipulators Through Kinesthetic Coupling," Computers in Mechanical Engineering NT Control No. MPO-17851; JPL Case No. 5348 Attachment, pp. 48-61, (Jul. 1983).

Townsend "Model-X Force-reflecting Hand Controller," NT Control No. MPO-17851; JPL Case No. 5348 Attachment, pp. 1-17, (Aug. 20, 1987).

Kotoku, "A Predictive Display with Force Feedback and Its Application to Remote Manipulation System with Transmission Time Delay," 0-7803-0737-2/92 1992 © IEEE, pp. 239-246, (Jul. 7-10, 1992).

Kotoku et al., "Environment Modelling for the Interactive Display (EMID) used in Telerobotic Systems,"0 IEEE Cat. No. 91TH0375-6, pp 999-1004, (Nov. 3-5, 1991).

Hirota, et al., "Development of Surface Display," 0-7803-1363-1/93 © 1993 IEEE, pp. 256-262, (1993).

Ouh-Young, "Force Display in Molecular Docking," Order No. 9034744, p. 1-369, (1990).

Tadros, Control System Design for a Three Degree of Freedom Virtual Environment Simulator Using Motor/Brake Pair Actuators, MIT Archive © Massachusetts Institute of Technology, pp. 1-66, (Feb. 1990).

Caldwell et al., "Enhanced Tactile Feedback (Tele-Taction) Using a Multi-Functional Sensory System," 1060-4729/93, pp. 955-960, (1993).

Adelstein, "Design and Implementation of a Force Reflecting Manipulandum for Manual Control research," DSC-vol. 42, Advances in Robotics, Edited by H. Kazerooni, pp. 1-12, (1992).

Gotow et al., "Controlled Impedance Test Apparatus for Studying Human Interpretation of Kinesthetic Feedback," WA11-11:00, pp. 332-337.

Stanley et al., "Computer Simulation of Interacting Dynamic Mechanical Systems Using Distributed Memory Parallel Processors," DSC-vol. 42, Advances in Robotics, pp. 55-61, (1992).

Russo, "Controlling Dissipative Magnetic Particle Brakes in Force Reflective Devices," DSC-vol. 42, Advances in Robotics, pp. 63-70, (1992).

Fukumoto et al., "Active Click: Tactile Feedback for Touch Panels," NTT DoCoMo CHI 2001, pp. 1-3, (Apr. 2001).

Wright, "A Manufacturing Hand," ISSN 0738-5845/85 (704), pp. 13-23, (1985).

Kontarinis et al., "Display of High-Frequency Tactile Information Teleoperators," Telemanipulator Technology and Space Telerobotics, Won S. Kim, Editor, Proc. SPIE vol. 2057, pp. 40-50, Sep. 7-9, 1993.

Patrick et al., "Design and Testing of A Non-reactive, Fingertip, Tactile Display for Interaction with Remote Environments," Cooperative Intelligent Robotics in Space, Rui J. deFigueiredo et al., Editor, Proc. SPIE vol. 1387, pp. 215-222, 1990.

Adelstein, "A Virtual Environment System For The Study of Human Arm Tremor," Ph.D. Dissertation, Dept. of Mechanical Engineering, MIT, Jun. 1989.

Bejczy, "Sensors, Controls, and Man-Machine Interface for Advanced Teleoperation," Science, vol. 208, No. 4450, pp. 1327-1335, 1980.

Bejczy et al., "Generalization of Bilateral Force-Reflecting Control of Manipulators," Proceedings Of Fourth CISM-IFToMM, Sep. 8-12, 1981.

McAffee et al., "Teleoperator Subsystem/Telerobot Demonstrator: Force Reflecting Hand Controller Equipment Manual," JPL D-5172, pp. 1-50, A1-A36, B1-B5, C1-C36, Jan. 1988.

Minsky, "Computational Haptics: The Sandpaper System for Synthesizing Texture for a Force-Feedback Display," Ph.D. Dissertation, MIT, Jun. 1995.

Jacobsen et al., "High Performance, Dextrous Telerobotic Manipulator With Force Reflection," Intervention/ROV '91 Conference & Exposition, Hollywood, Florida, May 21-23, 1991.

Shimoga, "Finger Force and Touch Feedback Issues in Dexterous Telemanipulation," Proceedings of Fourth Annual Conference on Intelligent Robotic Systems for Space Exploration, Rensselaer Polytechnic Institute, Sep. 30-Oct. 1, 1992.

IBM Technical Disclosure Bulletin, "Mouse Ball-Actuating Device With Force and Tactile Feedback," vol. 32, No. 9B, Feb. 1990.

Terry et al., "Tactile Feedback In A Computer Mouse," Proceedings of Fourteenth Annual Northeast Bioengineering Conference, University of New Hampshire, Mar. 10-11, 1988.

Howe, "A Force-Reflecting Teleoperated Hand System for the Study of Tactile Sensing in Precision Manipulation," Proceedings of the 1992 IEEE International Conference on Robotics and Automation, Nice, France, May 1992.

Eberhardt et al., "OMAR—A Haptic display for speech perception by deaf and deaf-blind individuals," IEEE Virtual Reality Annual International Symposium, Seattle, WA, Sep. 18-22, 1993.

Rabinowitz et al., "Multidimensional tactile displays: Identification of vibratory intensity, frequency, and contactor area," Journal of The Acoustical Society of America, vol. 82, No. 4, Oct. 1987.

Bejczy et al., "Kinesthetic Coupling Between Operator and Remote Manipulator," International Computer Technology Conference, The American Society of Mechanical Engineers, San Francisco, CA, Aug. 12-15, 1980.

Bejczy et al., "A Laboratory Breadboard System For Dual-Arm Teleoperation," SOAR '89 Workshop, JSC, Houston, TX, Jul. 25-27, 1989.

Ouh-Young et al., "A Low-Cost Force Feedback Joystick and Its Use in PC Video Games," IEEE Transactions on Consumer Electronics, vol. 41, No. 3, Aug. 1995.

Marcus, "Touch Feedback in Surgery," Proceedings of Virtual Reality and Medicine The Cutting Edge, Sep. 8-11, 1994.

Bejczy, et al., "Universal Computer Control System (UCCS) For Space Telerobots," CH2413-3/87/0000/0318501.00 1987 IEEE, 1987.

Aukstakalnis, et al., "Silicon Mirage: The Art and Science of Virtual Reality," ISBN 0-938151-82-7, pp. 129-180, 1992.

Eberhardt et al., "Including Dynamic Haptic Perception by The Hand: System Description and Some Results," DSC-vol. 55-1, Dynamic Systems and Control: vol. 1, ASME 1994.

Gobel et al., "Tactile Feedback Applied to Computer Mice," International Journal of Human-Computer Interaction, vol. 7, No. 1, pp. 1-24, 1995.

Pimentel et al., "Virtual Reality: through the new looking glass," 2$^{nd}$ Edition; McGraw-Hill, ISBN 0-07-050167-X, pp. 41-202, 1994.

"Cyberman Technical Specification," Logitech Cyberman SWIFT Supplement, Apr. 5, 1994.

Ouhyoung et al., "The Development of A Low-Cost Force Feedback Joystick and Its Use in the Virtual Reality Environment," Proceedings of the Third Pacific Conference on Computer Graphics and Applications, Pacific Graphics '95, Seoul, Korea, Aug. 21-24, 1995.

Kaczmarek et al., "Tactile Displays," Virtual Environment Technologies.

Scannell, "Taking a Joystick Ride," Computer Currents, Boston Edition, vol. 9, No. 11, Nov. 1994.

"Component Maintenance Manual With Illustrated Parts List, Coaxial Control Shaker Part No. C-25502," Safe Flight Instrument Corporation, Revised Jan. 28, 2002 (3 pages).

"Technical Manual Overhaul Instructions With Parts Breakdown, Coaxial Control Shaker Part No. C-25502," Safe Flight Instrument Corporation, Revised Jul. 15, 1980 (23 pages).

Patrick, "Design, Construction, and Testing of a Fingertip Tactile Display for Interaction with Virtual and Remote Environments," *Master of Science Thesis*, MIT, Aug. 1990, archived Nov. 8, 1990.

Calder, "Design of A Force-Feedback Touch-Introducing Actuator For Teleoperator Robot Control," *Bachelor of Science Thesis*, MIT, May 1983, archived Jun. 23, 1983.

Wiker, "Teletouch Display Development: Phase 1 Report," *Technical Report 130*, Naval Ocean Systems Center, San Diego, Jul. 1988.

Bliss, "Optical-to-Tactile Image Conversion for the Blind," *IEEE Transactions on Man-Machine Systems*, vol. MMS-11, No. 1, Mar. 1970.

Johnson, "Shape-Memory Alloy Tactile Feedback Actuator," *Armstrong Aerospace Medical Research Laboratory*, AAMRL-TR-90-039, Aug. 1990.

Kontarinis et al., "Tactile Display of Vibratory Information in Teleoperation and Virtual Environments," PRESENCE, 4(4):387-402, Harvard Univ., 1995.

Lake, "Cyberman from Logitech," at http://www.ibiblio.org/GameBytes/issue21/greviews/cyberman.html, 1994.

Noll, "Man-Machine Tactile," *SID Journal*, Jul./Aug. 1972 Issue.

Rosenberg, "Virtual Fixtures: Perceptual Overlays Enhance Operator Performance In Telepresence Tasks," *Ph.D. Dissertation*, Stanford University, Jun. 1994.

Rosenberg, Louis B., "The Use of Virtual Fixtures as Perceptual Overlays to Enhance Operator Performance in Remote Environments," Air Force Material Command, Sep. 1992, pp. 1-42.

Burdea, Grigore et al., " A Portable Dextrous Master with Force Feedback," Presence: Teleoperators and Virtual Environments, MIT Press, Jun. 1991.

Meyer, Kenneth et al., "A Survey of Position Trackers," Presence, vol. 1, No. 2, Spring 1992, pp. 173-200.

\* cited by examiner

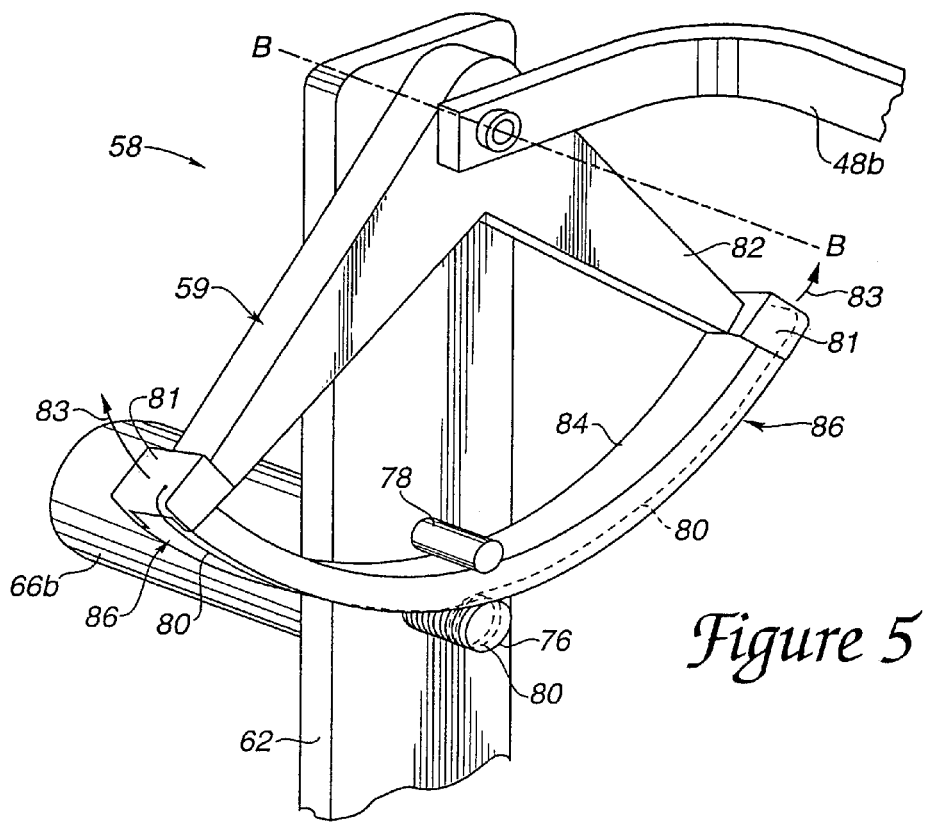
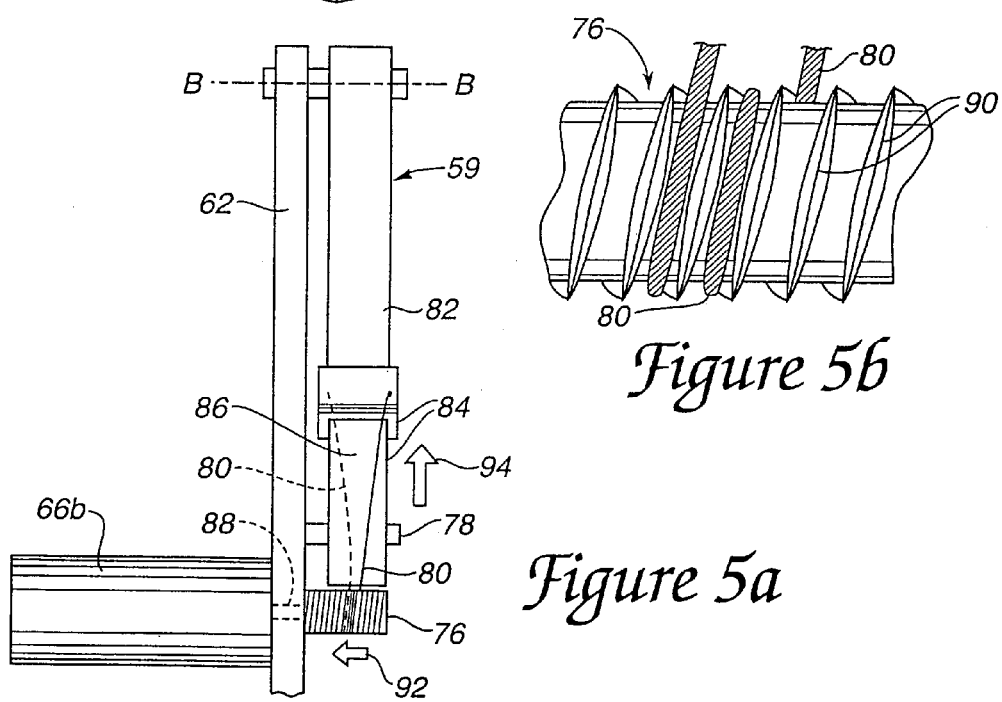

LAPAROSCOPIC SIMULATION INTERFACE

This application is a continuation of prior application Ser. No. 08/870,956 filed on Jun. 6, 1997, now U.S. Pat. No. 6,246,390, which is a continuation of application Ser. No. 08/374,288, filed on Jan. 18, 1995, now U.S. Pat. No. 5,731,804, both of which are incorporated herein by reference in their entireties.

This invention was made with Government support under Contract Number III-9361801 awarded by the National Science Foundation, and Contract Number DE-FG03-94ER86008 awarded by the Department of Energy. The Government has certain rights in this invention.

BACKGROUND OF THE INVENTION

The present invention relates generally to interface devices between humans and computers, and more particularly to computer input devices having three-dimensional input.

Virtual reality computer systems provide users with the illusion that they are part of a "virtual" environment. A virtual reality system will typically include a computer processor, such as a personal computer or workstation, specialized virtual reality software, and virtual reality I/O devices such as head mounted displays, sensor gloves, three dimensional ("3D") pointers, etc.

One common use for virtual reality computer systems is for training. In many fields, such as aviation and vehicle and systems operation, virtual reality systems have been used successfully to allow a user to learn from and experience a realistic "virtual" environment. The appeal of using virtual reality computer systems for training relates, in part, to the ability of such systems to allow trainees the luxury of confidently operating in a highly realistic environment and making mistakes without "real world" consequences. Thus, for example, a trainee pilot or automobile driver can learn to operate a vehicle using a virtual reality simulator without concern for accidents that would cause injury, death and/or property damage in the real world. Similarly, operators of complex systems, e.g., nuclear power plants and weapons systems, can safely practice a wide variety of training scenarios that would risk life or property if performed in reality.

For example, a virtual reality computer system can allow a doctor-trainee or other human operator or user to "manipulate" a scalpel or probe within a computer-simulated "body", and thereby perform medical procedures on a virtual patient. In this instance, the I/O device which is typically a 3D pointer, stylus, or the like is used to represent a surgical instrument such as a scalpel or probe. As the "scalpel" or "probe" moves within a provided space or structure, results of such movement are updated and displayed in a body image displayed on the screen of the computer system so that the operator can gain the experience of performing such a procedure without practicing on an actual human being or a cadaver.

In other applications, virtual reality computers systems allow a user to handle and manipulate the controls of complicated and expensive vehicles and machinery. For example, a pilot or astronaut in training can operate a fighter aircraft or spacecraft by manipulating controls such as a control joystick and other buttons and view the results of controlling the aircraft on a virtual reality simulation of the aircraft flying. In yet other applications, a user can manipulate objects and tools in the real world, such as a stylus, and view the results of the manipulation in a virtual reality world with a "virtual stylus" viewed on a screen, in 3-D goggles, etc.

For virtual reality systems to provide a realistic (and therefore effective) experience for the user, sensory feedback and manual interaction should be as natural as possible. As virtual reality systems become more powerful and as the number of potential applications increases, there is a growing need for specific human/computer interface devices which allow users to interface with computer simulations with tools that realistically emulate the activities being represented within the virtual simulation. Such procedures as laparoscopic surgery, catheter insertion, and epidural analgesia should be realistically simulated with suitable human/computer interface devices if the doctor is to be properly trained. Similarly, a user should be provided with a realistic interface for manipulating controls or objects in a virtual reality simulation to gain useful experience.

While the state of the art in virtual simulation and medical imaging provides a rich and realistic visual feedback, there is a great need for new human/computer interface tools which allow users to perform natural manual interactions with the computer simulation. For medical simulation, there is a strong need to provide doctors with a realistic mechanism for performing the manual activities associated with medical procedures while allowing a computer to accurately keep track of their actions. There is also a need in other simulations to provide virtual reality users with accurate and natural interfaces for their particular tasks.

In addition to sensing and tracking a user's manual activity and feeding such information to the controlling computer to provide a 3D visual representation to the user, a human interface mechanism should also provide force or tactile ("haptic") feedback to the user. The need for the user to obtain realistic tactile information and experience tactile sensation is extensive in many kinds of simulation. For example, in medical/surgical simulations, the "feel" of a probe or scalpel simulator is important as the probe is moved within the simulated body. It would invaluable to a medical trainee to learn how an instrument moves within a body, how much force is required depending on the operation performed, the space available in a body to manipulate an instrument, etc. In simulations of vehicles or equipment, force feedback for controls such as a joystick can be necessary to realistically teach a user the force required to move the joystick when steering in specific situations, such as in a high acceleration environment of an aircraft. In virtual world simulations where the user can manipulate objects, force feedback is necessary to realistically simulate physical objects; for example, if a user touches a pen to a table, the user should feel the impact of the pen on the table. An effective human interface not only acts as an input device for tracking motion, but also as an output device for producing realistic tactile sensations. A "high bandwidth" interface system, which is an interface that accurately responds to signals having fast changes and a broad range of frequencies as well as providing such signals accurately to a control system, is therefore desirable in these and other applications.

There are number of devices that are commercially available for interfacing a human with a computer for virtual reality simulations. There are, for example, such 2-dimensional input devices such as mice, trackballs, and digitizing tablets. However, 2-dimensional input devices tend to be awkward and inadequate to the task of interfacing with 3-dimensional virtual reality simulations.

Other 3-dimensional interface devices are available. A 3-dimensional human/computer interface tool sold under the trademark Immersion PROBE™ is marketed by Immersion Human Interface Corporation of Santa Clara, Calif., and allows manual control in 3-dimensional virtual reality computer environments. A pen-like stylus allows for dexterous 3-dimensional manipulation, and the position and orientation of the stylus is communicated to a host computer. The Immersion PROBE has six degrees of freedom which convey spatial coordinates (x, y, z) and orientation (roll, pitch, yaw) of the stylus to the host computer.

While the Immersion PROBE is an excellent 3-dimensional interface tool, it may be inappropriate for certain virtual reality simulation applications. For example, in some of the aforementioned medical simulations three or four degrees of freedom of a 3-dimensional human/computer interface tool is sufficient and, often, more desirable than five or six degrees of freedom because it more accurately mimics the real-life constraints of the actual medical procedure. More importantly, the Immersion PROBE does not provide force feedback to a user and thus does not allow a user to experience an entire sensory dimension in virtual reality simulations.

In typical multi-degree of freedom apparatuses that include force feedback, there are several disadvantages. Since actuators which supply force feedback tend to be heavier and larger than sensors, they would provide inertial constraints if added to a device such as the Immersion PROBE. There is also the problem of coupled actuators. In a typical force feedback device, a serial chain of links and actuators is implemented to achieve multiple degrees of freedom in a desired object positioned at the end of the chain, i.e., each actuator is coupled to the previous actuator. The user who manipulates the object must carry the inertia of all of the subsequent actuators and links except for the first actuator in the chain, which is grounded. While it is possible to ground all of the actuators in a serial chain by using a complex transmission of cables or belts, the end result is a low stiffness, high friction, high damping transmission which corrupts the bandwidth of the system, providing the user with an unresponsive and inaccurate interface. These types of interfaces also introduce tactile "noise" to the user through friction and compliance in signal transmission and limit the degree of sensitivity conveyed to the user through the actuators of the device.

Other existing devices provide force feedback to a user. In U.S. Pat. No. 5,184,319, by J. Kramer, an interface is described which provides force and texture information to a user of a computer system. The interface consists of an glove or "exoskeleton" which is worn over the user's appendages, such as fingers, arms, or body. Forces can be applied to the user's appendages using tendon assemblies and actuators controlled by a computer system to simulate force and textual feedback. However, the system described by Kramer is not easily applicable to simulation environments such as those mentioned above where an object is referenced in 3D space and force feedback is applied to the object. The forces applied to the user in Kramer are with reference to the body of the user; the absolute location of the user's appendages are not easily calculated. In addition, the exoskeleton devices of Kramer can be cumbersome or even dangerous to the user if extensive devices are worn over the user's appendages. Furthermore, the devices disclosed in Kramer are complex mechanisms in which many actuators must be used to provide force feedback to the user.

Therefore, a less complex, more compact, and less expensive alternative to a human/computer interface tool having force feedback, lower inertia, higher bandwidth, and less noise is desirable for certain applications.

SUMMARY OF THE INVENTION

The present invention provides a human/computer interface apparatus which can provide from two to six degrees of freedom and highly realistic force feedback to a user of the apparatus. The preferred apparatus includes a gimbal mechanism and linear axis member which provide three degrees of freedom to an object coupled to the apparatus and held by the user. The structure of the apparatus permits transducers to be positioned such that their inertial contribution to the system is very low. In addition, a capstan drive mechanism provides mechanical advantage in applying force feedback to the user, smooth motion, and reduction of friction, compliance, and backlash of the system. The present invention is particularly well suited to simulations of medical procedures using specialized tools and moving an object such as a stylus or joystick in three-dimensional simulations.

An apparatus of the present invention for interfacing the motion of an object with an electrical system includes a gimbal mechanism that provides two revolute degrees of freedom to an object about two axes of rotation. In the preferred embodiment, the gimbal mechanism is a closed loop five-member linkage including a ground member coupled to a ground surface, first and second extension members, each being coupled to the ground member, and first and second central members, the first central member having an end coupled to the first extension member and the second central member having an end coupled to the second extension member.

A linear axis member is coupled to the gimbal mechanism at the intersection of the two central members, which is at the intersection of the two axes of rotation. The linear axis member is capable of being translated along a third axis to provide a third degree of freedom. The user object is coupled to the linear axis member and is thus translatable along the third axis so that the object can be moved along all three degrees of freedom. Transducers are also coupled between members of the gimbal mechanism and linear axis member to provide an electromechanical interface between the object and the electrical system.

In one embodiment, the linear axis member can be rotated about its lengthwise axis to provide a fourth degree of freedom. Four transducers are preferably provided, each transducer being associated with a degree of freedom. The transducers for the first three degrees of freedom include sensors and actuators, and the transducer for the fourth degree of freedom preferably includes a sensor. The sensors are preferably digital encoders and the actuators are basket wound DC servo motors. The sensors sense the positions of the object along the respective degrees of freedom and provide the sensory information to a digital processing system such as a computer. The actuators impart forces along the respective degrees of freedom in response to electrical signals produced by the computer.

In the preferred embodiment, a capstan drive mechanism is coupled between an actuator and the gimbal mechanism for each degree of freedom of the gimbal mechanism. The capstan drive mechanism transmits the force generated by the transducer to the gimbal mechanism and transmits any forces generated by the user on the gimbal mechanism to the transducer. In addition, a capstan drive mechanism is preferably used between the linear axis member and a transducer to transmit force along the third degree of freedom. The capstan drive mechanisms each preferably include a rotating capstan drum rotatably coupled to the gimbal mechanism, where the capstan drum is coupled to a pulley by a cable and the transducer is coupled to the pulley.

In another embodiment, a floating gimbal mechanism is coupled to the linear axis member to provide fifth and sixth degrees of freedom to an object coupled to the floating gimbal mechanism. Fifth and sixth degree of freedom transducers are coupled to the floating gimbal mechanism to sense the position of the object along the fifth and sixth degrees of freedom. In one embodiment, the handle or grip of a medical tool such as a laparoscope is used as the object in a medical procedure simulation. In other embodiments, a stylus or a joystick is used as the object.

The gimbal mechanism of the present invention provides a structure allowing transducers associated with two degrees of freedom to be decoupled from each other and instead be coupled to a ground surface. This allows the weight of the transducers to contribute a negligible inertia to the system, providing a low friction, high bandwidth motion system. The addition of a linear axis member and transducer positioned near the center of rotation of the gimbal mechanism allows a third degree of freedom to be added with minimal inertia. The present invention also includes capstan drive mechanisms coupled between the transducers and moving components of the apparatus. The capstan drive provides mechanical advantage while allowing smooth movement to be achieved and providing negligible friction and backlash to the system. These advantages allow a computer system to have more complete and realistic control over force feedback sensations experienced by a user of the apparatus.

These and other advantages of the present invention will become apparent to those skilled in the art upon a reading of the following specification of the invention and a study of the several figures of the drawing.

BRIEF DESCRIPTION OF THE DRAWINGS

FIG. 5 is a perspective detailed view of a capstan drive mechanism used for two degrees of motion in the present invention;

FIG. 5a is a side elevational view of the capstan drive mechanism shown in FIG. 5;

FIG. 5b is a detailed side view of a pulley and cable of the capstan drive mechanism of FIG. 5;

DETAILED DESCRIPTION OF PREFERRED EMBODIMENTS

Figure 1:
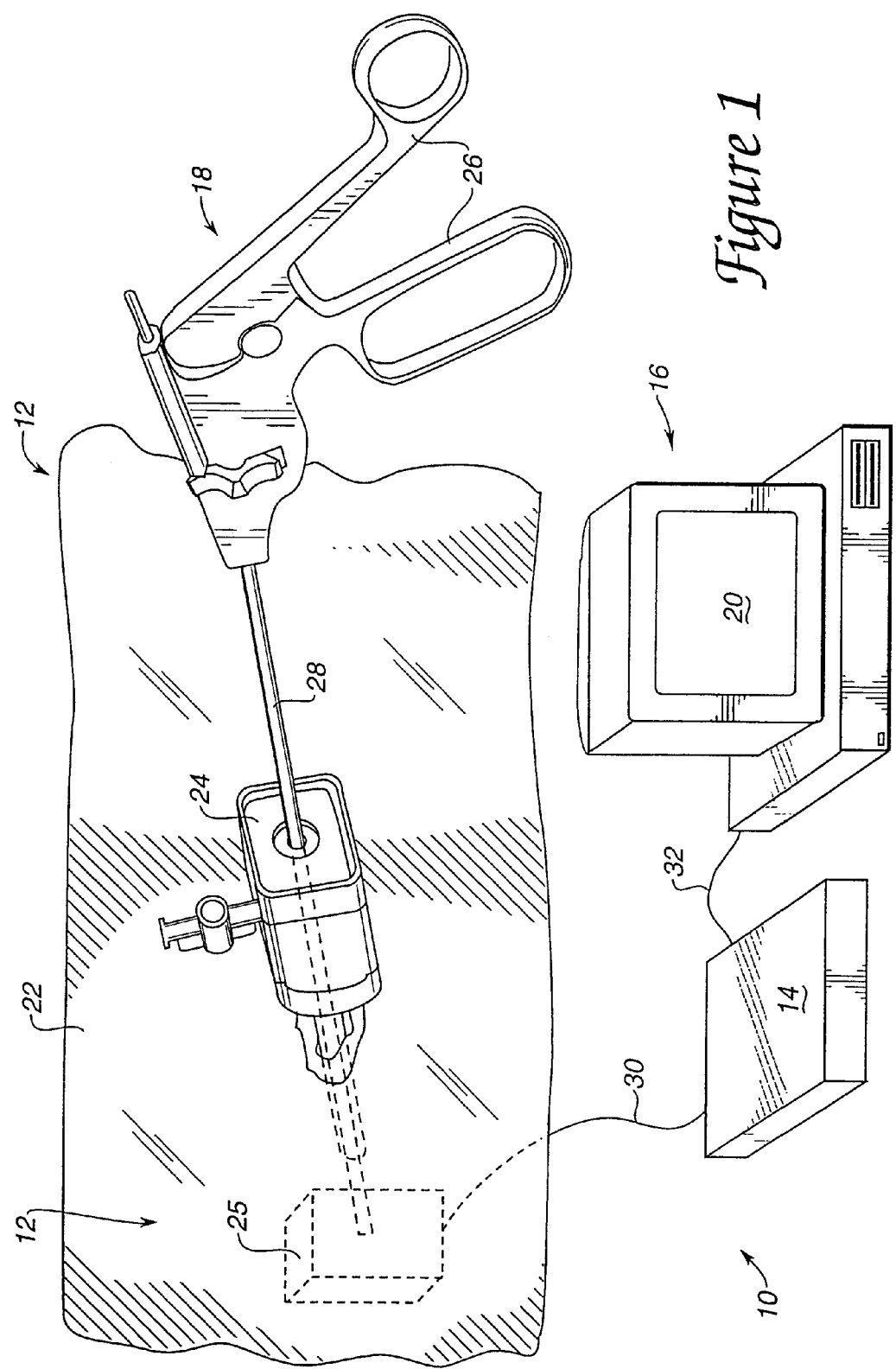
FIG. 1 is a perspective view of a virtual reality system which employs an apparatus of the present invention to interface a laparoscope tool handle with a computer system.

In FIG. 1, a virtual reality system 10 used to simulate a medical procedure includes a human/computer interface apparatus 12, an electronic interface 14, and a computer 16. The illustrated virtual reality system 10 is directed to a virtual reality simulation of a laparoscopic surgery procedure. The software of the simulation is not a part of this invention and thus will not be discussed in any detail. However, such software is commercially available as, for example, Teleos™ from High Techsplanations of Rockville, Md. Suitable software drivers which interface such simulation software with computer input/output (I/O) devices are available from Immersion Human Interface Corporation of Santa Clara, Calif.

The handle 26 of a laparoscopic tool 18 used in conjunction with the present invention is manipulated by an operator and virtual reality images are displayed on a screen 20 of the digital processing system in response to such manipulations. Preferably, the digital processing system is a personal computer or workstation, such as an IBM-PC AT or Macintosh personal computer, or a SUN or Silicon Graphics workstation. Most commonly, the digital processing system is a personal computer which operates under the MS-DOS operating system in conformance with an IBM PC AT standard.

The human/interface apparatus 12 as illustrated herein is used to simulate a laparoscopic medical procedure. In addition to the handle of a standard laparoscopic tool 18, the human/interface apparatus 12 may include a barrier 22 and a standard laparoscopic trocar 24 (or a facsimile of a trocar). The barrier 22 is used to represent portion of the skin covering the body of a patient. Trocar 24 is inserted into the body of the virtual patient to provide an entry and removal point from the body of the patient for the laparoscopic tool 18, and to allow the manipulation of the laparoscopic tool. Laparoscopic tools and trocars 24 are commercially available from sources such as U.S. Surgical of Connecticut. Barrier 22 and trocar 24 can be omitted from apparatus 12 in other embodiments. Preferably, the laparoscopic tool 18 is modified; in the preferred embodiment, the shaft is replaced by a linear axis member of the present invention, as described below. In other embodiments, the end of the shaft of the tool (such as any cutting edges) can be removed. The end of the laparoscopic tool 18 is not required for the virtual reality simulation, and is removed to prevent any potential damage to persons or property. An apparatus 25 for interfacing mechanical input and output is shown within the "body" of the patient in phantom lines.

The laparoscopic tool 18 includes a handle or "grip" portion 26 and a shaft portion 28. The shaft portion is an elongated mechanical object and, in particular, is an elongated cylindrical object, described in greater detail below. In one embodiment, the present invention is concerned with tracking the movement of the shaft portion 28 in three-dimensional space, where the movement has been constrained such that the shaft portion 28 has only three or four free degrees of motion. This is a good simulation of the real use of a laparoscopic tool 18 in that once it is inserted into a trocar 24 and through the gimbal apparatus 25, it is limited to about four degrees of freedom. More particularly, the shaft 28 is constrained at some point of along its length such that it can move with four degrees of freedom within the patient's body.

While one embodiment of the present invention will be discussed with reference to the laparoscopic tool 18, it will be appreciated that a great number of other types of objects can be used with the method and apparatus of the present invention. In fact, the present invention can be used with any mechanical object where it is desirable to provide a human/computer interface with three to six degrees of freedom. Such objects may include endoscopic or other similar surgical tools used in medical procedures, catheters, hypodermic needles, wires, fiber optic bundles, styluses, joysticks, screw drivers, pool cues, etc. Some of these other objects are described in detail subsequently.

The electronic interface 14 is a component of the human/computer interface apparatus 12 and couples the apparatus 12 to the computer 16. More particularly, interface 14 is used in preferred embodiments to couple the various actuators and sensors contained in apparatus 12 (which actuators and sensors are described in detail below) to computer 16. A suitable interface 14 is described in detail with reference to FIG. 9.

The electronic interface 14 is coupled to mechanical apparatus 25 of the apparatus 12 by a cable 30 and is coupled to the computer 16 by a cable 32. In other embodiments, signal can be sent to and from interface 14 and computer 16 by wireless transmission and reception. In some embodiments of the present invention, interface 14 serves solely as an input device for the computer 16. In other embodiments of the present invention, interface 14 serves solely as an output device for the computer 16. In preferred embodiments of the present invention, the interface 14 serves as an input/output (I/O) device for the computer 16.

Figure 2:
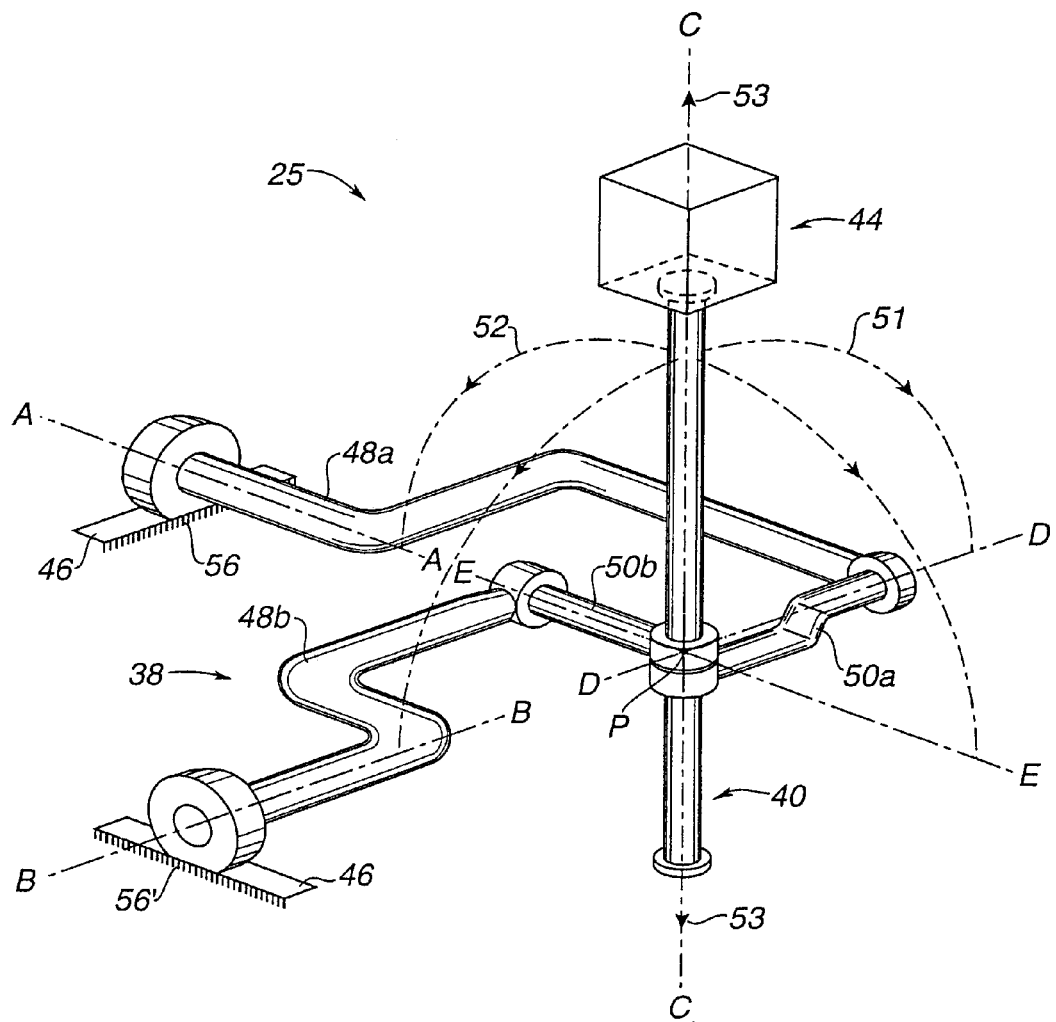
FIG. 2 is a schematic diagram of a mechanical apparatus of the present invention for providing mechanical input and output to a computer system.

In FIG. 2, a schematic diagram of mechanical apparatus 25 for providing mechanical input and output in accordance with the present invention is shown. Apparatus 25 includes a gimbal mechanism 38 and a linear axis member 40. A user object 44 is preferably coupled to linear axis member 40.

Gimbal mechanism 38, in the described embodiment, provides support for apparatus 25 on a grounded surface 56 (schematically shown as part of member 46). Gimbal mechanism 38 is preferably a five-member linkage that includes a ground member 46, extension members 48a and 48b, and central members 50a and 50b. Ground member 46 is coupled to a base or surface which provides stability for apparatus 25. Ground member 46 is shown in FIG. 2 as two separate members coupled together through grounded surface 56. The members of gimbal mechanism 38 are rotatably coupled to one another through the use of bearings or pivots, wherein extension member 48a is rotatably coupled to ground member 46 and can rotate about an axis A, central member 50a is rotatably coupled to extension member 48a and can rotate about a floating axis D, extension member 48b is rotatably coupled to ground member 46 and can rotate about axis B, central member 50b is rotatably coupled to extension member 48b and can rotate about floating axis E, and central member 50a is rotatably coupled to central member 50b at a center point P at the intersection of axes D and E. The axes D and E are "floating" in the sense that they are not fixed in one position as are axes A and B. Axes A and B are substantially mutually perpendicular. As used herein, "substantially perpendicular" will mean that two objects or axis are exactly or almost perpendicular, i.e. at least within five degrees or ten degrees of perpendicular, or more preferably within less than one degree of perpendicular. Similarly, the term "substantially parallel" will mean that two objects or axis are exactly or almost parallel, i.e. are at least within five or ten degrees of parallel, and are preferably within less than one degree of parallel.

Gimbal mechanism 38 is formed as a five member closed chain. Each end of one member is coupled to the end of a another member. The five-member linkage is arranged such that extension member 48a, central member 50a, and central member 50b can be rotated about axis A in a first degree of freedom. The linkage is also arranged such that extension member 48b, central member 50b, and central member 50a can be rotated about axis B in a second degree of freedom.

Linear axis member 40 is preferably an elongated rod-like member which is coupled to central member 50a and central member 50b at the point of intersection P of axes A and B. As shown in FIG. 1, linear axis member 40 can be used as shaft 28 of user object 44. In other embodiments, linear axis member 40 is coupled to a different object. Linear axis member 40 is coupled to gimbal mechanism 38 such that it extends out of the plane defined by axis A and axis B. Linear axis member 40 can be rotated about axis A by rotating extension member 48a, central member 50a, and central member 50b in a first revolute degree of freedom, shown as arrow line 51. Member 40 can also be rotated about axis B by rotating extension member 50b and the two central members about axis B in a second revolute degree of freedom, shown by arrow line 52. Being also translatably coupled to the ends of central members 50a and 50b, linear axis member 40 can be linearly moved along floating axis C, providing a third degree of freedom as shown by arrows 53. Axis C can, of course, be rotated about one or both axes A and B as member 40 is rotated about these axes.

Also preferably coupled to gimbal mechanism 38 and linear axis member 40 are transducers, such as sensors and actuators. Such transducers are preferably coupled at the link points between members of the apparatus and provide input to and output from an electrical system, such as computer 16. Transducers that can be used with the present invention are described in greater detail with respect to FIG. 2.

User object 44 is coupled to apparatus 25 and is preferably an interface object for a user to grasp or otherwise manipulate in three dimensional (3D) space. One preferred user object 44 is the grip 26 of a laparoscopic tool 18, as shown in FIG. 1. Shaft 28 of tool 18 can be implemented as part of linear axis member 40. Other examples of user objects are described in subsequent embodiments. User object 44 may be moved in all three degrees of freedom provided by gimbal mechanism 38 and linear axis member 40 and additional degrees of freedom as described below. As user object 44 is moved about axis A, floating axis D varies its position, and as user object 44 is moved about axis B, floating axis E varies its position.

Figure 3:
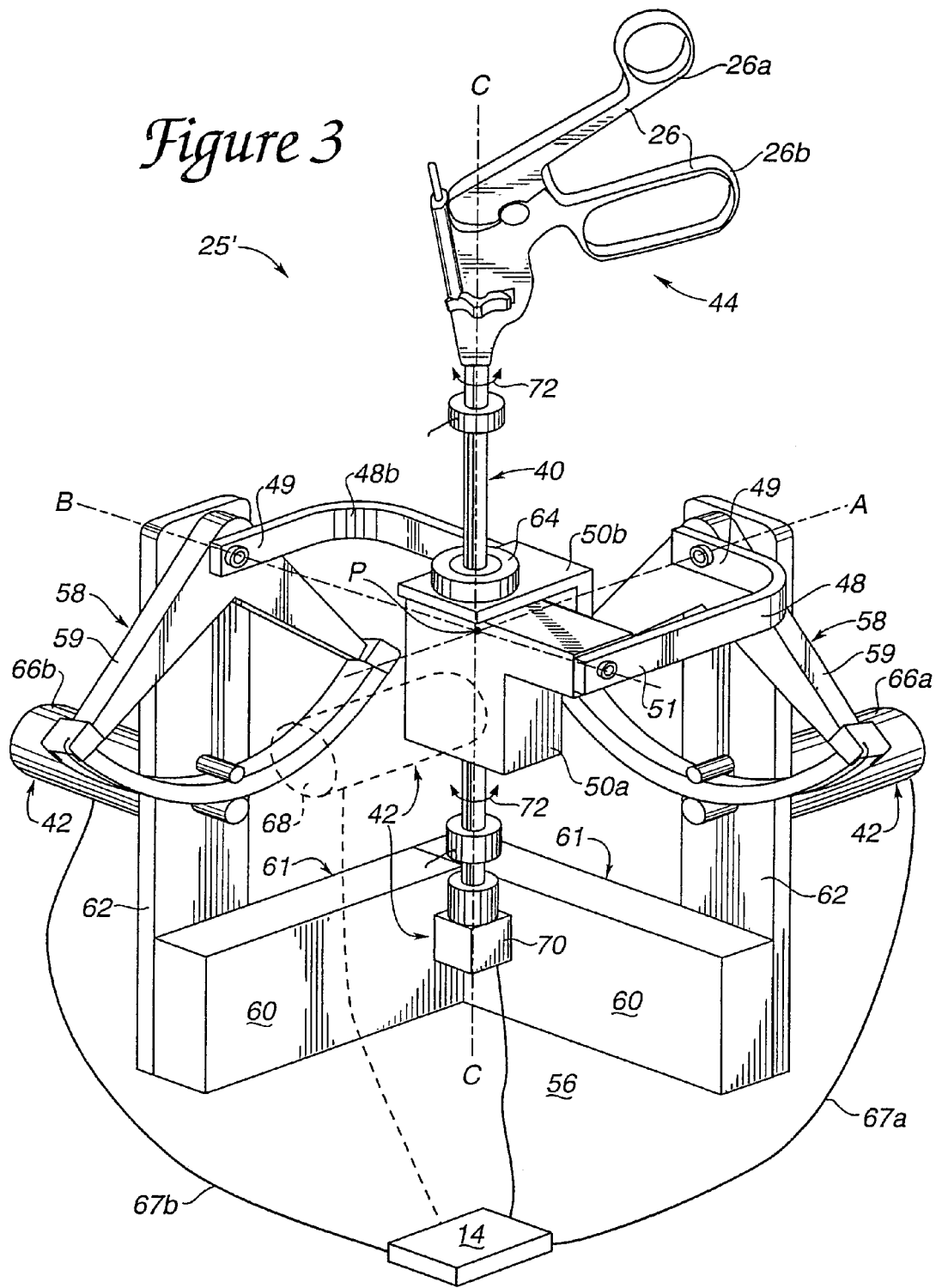
FIG. 3 is a perspective front view of a preferred embodiment of the mechanical apparatus of FIG. 2.
Figure 4:
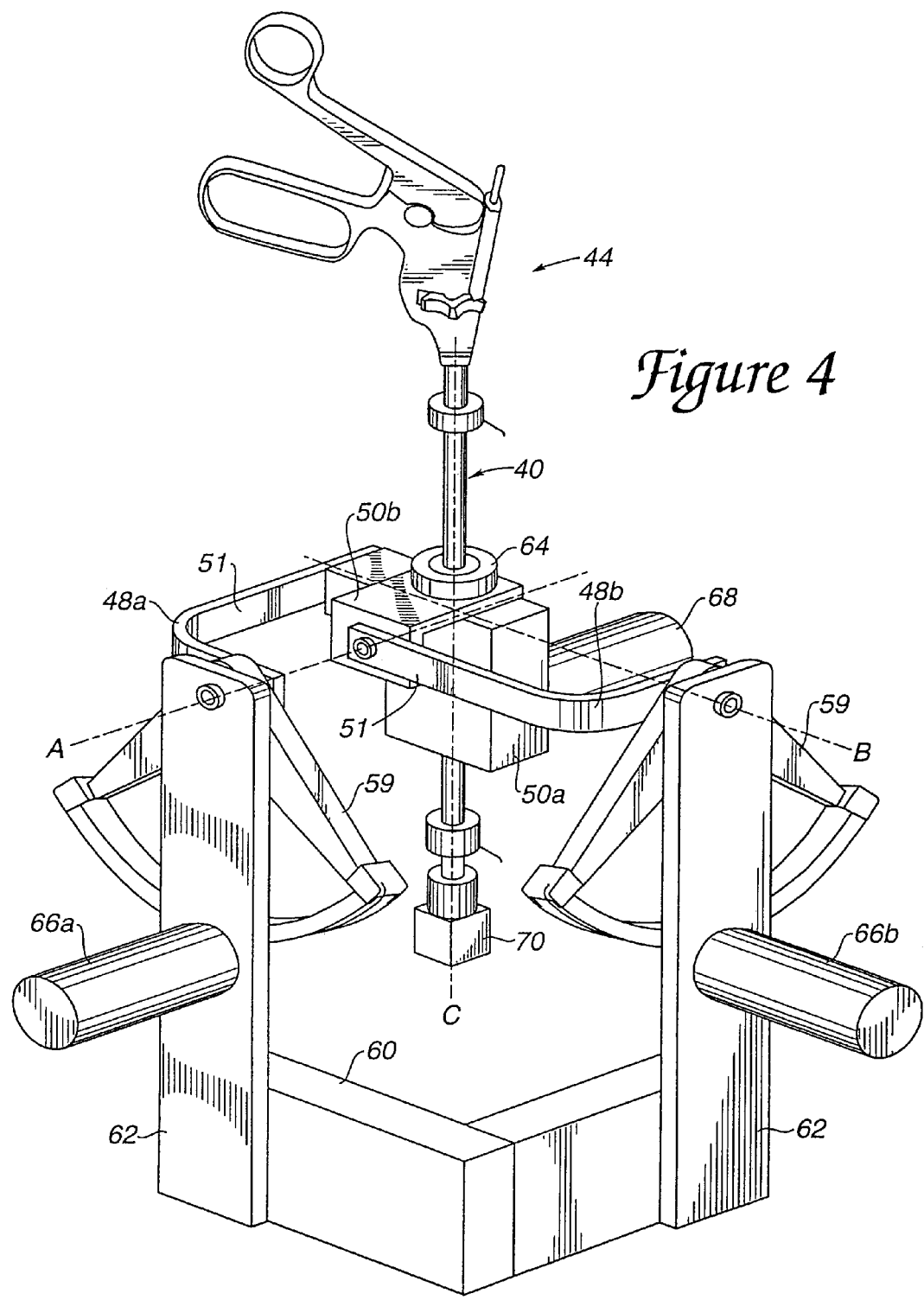
FIG. 4 is a perspective rear view of the embodiment of the mechanical apparatus of FIG. 3.

FIGS. 3 and 4 are perspective views of a specific embodiment of a mechanical apparatus 25' for providing mechanical input and output to a computer system in accordance with the present invention. FIG. 3 shows a front view of apparatus 25', and FIG. 4 shows a rear view of the apparatus. Apparatus 25' includes a gimbal mechanism 38, a linear axis member 40, and transducers 42. A user object 44, shown in this embodiment as a laparoscopic instrument having a grip portion 26, is coupled to apparatus 25'. Apparatus 25' operates in substantially the same fashion as apparatus 25 described with reference to FIG. 2.

Gimbal mechanism 38 provides support for apparatus 25' on a grounded surface 56, such as a table top or similar surface. The members and joints ("bearings") of gimbal mechanism 38 are preferably made of a lightweight, rigid, stiff metal, such as aluminum, but can also be made of other rigid materials such as other metals, plastic, etc. Gimbal mechanism 38 includes a ground member 46, capstan drive mechanisms 58, extension members 48a and 48b, central drive member 50a, and central link member 50b. Ground member 46 includes a base member 60 and vertical support members 62. Base member 60 is coupled to grounded surface 56 and provides two outer vertical surfaces 61 which are in a substantially perpendicular relation which each other. A vertical support member 62 is coupled to each of these outer surfaces of base member 60 such that vertical members 62 are in a similar substantially 90-degree relation with each other.

A capstan drive mechanism 58 is preferably coupled to each vertical member 62. Capstan drive mechanisms 58 are included in gimbal mechanism 38 to provide mechanical advantage without introducing friction, and backlash to the system. A capstan drum 59 of each capstan drive mechanism is rotatably coupled to a corresponding vertical support member 62 to form axes of rotation A and B, which correspond to axes A and B as shown in FIG. 1. The capstan drive mechanisms 58 are described in greater detail with respect to FIG. 5.

Extension member 48a is rigidly coupled to capstan drum 59 and is rotated about axis A as capstan drum 59 is rotated. Likewise, extension member 48b is rigidly coupled to the other capstan drum 59 and can be rotated about axis B. Both extension members 48a and 48b are formed into a substantially 90-degree angle with a short end 49 coupled to capstan drum 59. Central drive member 50a is rotatably coupled to a long end 51 of extension member 48a and extends at a substantially parallel relation with axis B. Similarly, central link member 50b is rotatably coupled to the long end of extension member 48b and extends at a substantially parallel relation to axis A (as better viewed in FIG. 4). Central drive member 50a and central link member 50b are rotatably coupled to each other at the center of rotation of the gimbal mechanism, which is the point of intersection P of axes A and B. Bearing 64 connects the two central members 50a and 50b together at the intersection point P.

Gimbal mechanism 38 provides two degrees of freedom to an object positioned at or coupled to the center point P of rotation. An object at or coupled to point P can be rotated about axis A and B or have a combination of rotational movement about these axes.

Linear axis member 40 is a cylindrical member that is preferably coupled to central members 50a and 50b at intersection point P. In alternate embodiments, linear axis member 40 can be a non-cylindrical member having a cross-section of, for example, a square or other polygon. Member 40 is positioned through the center of bearing 64 and through holes in the central members 50a and 50b. The linear axis member can be linearly translated along axis C, providing a third degree of freedom to user object 44 coupled to the linear axis member. Linear axis member 40 can preferably be translated by a transducer 42 using a capstan drive mechanism similar to capstan drive mechanism 58. The translation of linear axis member 40 is described in greater detail with respect to FIG. 6.

Transducers 42 are preferably coupled to gimbal mechanism 38 to provide input and output signals between mechanical apparatus 25' and computer 16. In the described embodiment, transducers 42 include two grounded transducers 66a and 66b, central transducer 68, and shaft transducer 70. The housing of grounded transducer 66a is preferably coupled to vertical support member 62 and preferably includes both an actuator for providing force in or otherwise influencing the first revolute degree of freedom about axis A and a sensor for measuring the position of object 44 in or otherwise influenced by the first degree of freedom about axis A, i.e., the transducer 66a is "associated with" or "related to" the first degree of freedom. A rotational shaft of actuator 66a is coupled to a pulley of capstan drive mechanism 58 to transmit input and output along the first degree of freedom. The capstan drive mechanism 58 is described in greater detail with respect to FIG. 5. Grounded transducer 66b preferably corresponds to grounded transducer 66a in function and operation. Transducer 66b is coupled to the other vertical support member 62 and is an actuator/sensor which influences or is influenced by the second revolute degree of freedom about axis B.

Grounded transducers 66a and 66b are preferably bi-directional transducers which include sensors and actuators. The sensors are preferably relative optical encoders which provide signals to measure the angular rotation of a shaft of the transducer. The electrical outputs of the encoders are routed to computer interface 14 via buses 67a and 67b and are detailed with reference to FIG. 9. Other types of sensors can also be used, such as potentiometers, etc.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the sensor's shaft is placed in a known position within the apparatus 25' and a calibration signal is provided to the system to provide the reference position mentioned above. All angles provided by the sensors are thereafter relative to that reference position. Such calibration methods are well known to those skilled in the art and, therefore, will not be discussed in any great detail herein.

Transducers 66a and 66b also preferably include actuators which, in the described embodiment, are linear current control motors, such as DC servo motors. These motors preferably receive current signals to control the direction and torque (force output) that is produced on a shaft; the control signals for the motor are produced by computer interface 14 on control buses 67a and 67b and are detailed with respect to FIG. 9. The motors may include brakes which allow the rotation of the shaft to be halted in a short span of time. A suitable transducer for the present invention including both an optical encoder and current controlled motor is a 20 W basket wound servo motor manufactured by Maxon of Burlingame, Calif.

In alternate embodiments, other types of motors can be used, such as a stepper motor controlled with pulse width modulation of an applied voltage, or pneumatic motors. However, the present invention is much more suited to the use of linear current controlled motors. This is because voltage pulse width modulation or stepper motor control involves the use of steps or pulses which can be felt as "noise" by the user. Such noise corrupts the virtual simulation. Linear current control is smoother and thus more appropriate for the present invention.

Passive actuators can also be used in transducers 66a, 66b and 68. Magnetic particle brakes or friction brakes can be used in addition to or instead of a motor to generate a passive resistance or friction in a degree of motion. An alternate preferred embodiment only including passive actuators may not be as realistic as an embodiment including motors; however, the passive actuators are typically safer for a user since the user does not have to fight generated forces.

In other embodiments, all or some of transducers 42 can include only sensors to provide an apparatus without force feedback along designated degrees of freedom. Similarly, all or some of transducers 42 can be implemented as actuators without sensors to provide only force feedback.

Central transducer 68 is coupled to central drive member 50a and preferably includes an actuator for providing force in the linear third degree of freedom along axis C and a sensor for measuring the position of object 44 along the third degree of freedom. The rotational shaft of central transducer 68 is coupled to a translation interface coupled to central drive member 50a which is described in greater detail with respect to FIG. 6. In the described embodiment, central transducer 68 is an optical encoder and DC servo motor combination similar to the actuators 66a and 66b described above.

The transducers 66a, 66b and 68 of the described embodiment are advantageously positioned to provide a very low amount of inertia to the user handling object 44. Transducer 66a and transducer 66b are decoupled, meaning that the transducers are both directly coupled to ground member 46 which is coupled to ground surface 56, i.e. the ground surface carries the weight of the transducers, not the user handling object 44. The weights and inertia of the transducers 66a and 66b are thus substantially negligible to a user handling and moving object 44. This provides a more realistic interface to a virtual reality system, since the computer can control the transducers to provide substantially all of the forces felt by the user in these degrees of motion. Apparatus 25' is a high bandwidth force feedback system, meaning that high frequency signals can be used to control transducers 42 and these high frequency signals will be applied to the user object with high precision, accuracy, and dependability. The user feels very little compliance or "mushiness" when handling object 44 due to the high bandwidth. In contrast, in typical prior art arrangements of multi-degree of freedom interfaces, one actuator "rides" upon another actuator in a serial chain of links and actuators. This low bandwidth arrangement causes the user to feel the inertia of coupled actuators when manipulating an object.

Central transducer 68 is positioned near the center of rotation of two revolute degrees of freedom. Though the transducer 68 is not grounded, its central position permits a minimal inertial contribution to the mechanical apparatus 25' along the provided degrees of freedom. A user manipulating object 44 thus will feel minimal internal effects from the weight of transducers 66a, 66b and 68.

Shaft transducer 70 preferably includes a sensor and is provided in the described embodiment to measure a fourth degree of freedom for object 44. Shaft transducer 70 is preferably positioned at the end of linear axis member 40 that is opposite to the object 44 and measures the rotational position of object 44 about axis C in the fourth degree of freedom, as indicated by arrow 72. Shaft transducer 70 is described in greater detail with respect to FIGS. 6 and 6b. Preferably, shaft transducer 72 is implemented using an optical encoder similar to the encoders described above. A suitable input transducer for use in the present invention is an optical encoder model SI marketed by U.S. Digital of Vancouver, Wash. In the described embodiment, shaft transducer 70 only includes a sensor and not an actuator. This is because for typical medical procedures, which is one intended application for the embodiment shown in FIGS. 3 and 4, rotational force feedback to a user about axis C is typically not required to simulate actual operating conditions. However, in alternate embodiments, an actuator such as a motor can be included in shaft transducer 70 similar to transducers 66a, 66b, and 68.

Object 44 is shown in FIGS. 3 and 4 as a grip portion 26 of a laparoscopic tool similar to the tool shown in FIG. 1. Shaft portion 28 is implemented as linear axis member 40. A user can move the laparoscopic tool about axes A and B, and can translate the tool along axis C and rotate the tool about axis C. The movements in these four degrees of freedom will be sensed and tracked by computer system 16. Forces can be applied preferably in the first three degrees of freedom by the computer system to simulate the tool impacting a portion of subject body, experiencing resistance moving through tissues, etc.

Optionally, additional transducers can be added to apparatus 25' to provide additional degrees of freedom for object 44. For example, a transducer can be added to grip 26 of laparoscopic tool 18 to sense when the user moves the two portions 26a and 26b relative to each other to simulate extending the cutting blade of the tool. Such a laparoscopic tool sensor is described in U.S. patent application Ser. No. 08/275,120, now Pat. No. 5,623,582, filed Jul. 14, 1994 and entitled "Method and Apparatus for Providing Mechanical I/O for Computer Systems" assigned to the assignee of the present invention and incorporated herein by reference in its entirety.

FIG. 5 is a perspective view of a capstan drive mechanism 58 shown in some detail. As an example, the drive mechanism 58 coupled to extension arm 48b is shown; the other capstan drive 58 coupled to extension arm 48a is substantially similar to the mechanism presented here. Capstan drive mechanism 58 includes capstan drum 59, capstan pulley 76, and stop 78. Capstan drum 59 is preferably a wedge-shaped member having leg portion 82 and a curved portion 84. Other shapes of member 59 can also be used. Leg portion 82 is pivotally coupled to vertical support member 62 at axis B (or axis A for the opposing capstan drive mechanism). Extension member 48b is rigidly coupled to leg portion 82 such that when capstan drum 59 is rotated about axis B, extension member 48b is also rotated and maintains the position relative to leg portion 82 as shown in FIG. 5. Curved portion 84 couples the two ends of leg portion 82 together and is preferably formed in an arc centered about axis B. Curved portion 84 is preferably positioned such that its bottom edge 86 is about 0.030 inches above pulley 76.

Cable 80 is preferably a thin metal cable connected to curved portion 84 of the capstan drum. Other types of durable cables, cords, wire, etc. can be used as well. Cable 80 is attached at a first end to curved portion 84 near an end of leg portion 82 and is drawn tautly against the outer surface 86 of curved portion 84. Cable 80 is wrapped around pulley 76 a number of times and is then again drawn tautly against outer surface 86. The second end of cable 80 is firmly attached to the other end of curved portion 84 near the opposite leg of leg portion 82. The cable transmits rotational force from pulley 76 to the capstan drum 59, causing capstan drum 59 to rotate about axis B as explained below. The cable also transmits rotational force from drum 59 to the pulley and transducer 66b. The tension in cable 80 should be at a level so that negligible backlash or play occurs between capstan drum 59 and pulley 76. Preferably, the tension of cable 80 can be adjusted by pulling more (or less) cable length through an end of curved portion 84. Caps 81 on the ends of curved portion 84 can be used to easily tighten cable 80. Each cap 81 is preferably tightly coupled to cable 80 and includes a pivot and tightening screw which allow the cap to move in a direction indicated by arrow 83 to tighten cable 80.

Capstan pulley 76 is a threaded metal cylinder which transfers rotational force from transducer 66b to capstan drum 59 and from capstan drum 59 to transducer 66b. Pulley 76 is rotationally coupled to vertical support member 62 by a shaft 88 (shown in FIG. 5a) positioned through a bore of vertical member 62 and rigidly attached to pulley 76. Transducer 66b is coupled to pulley 76 by shaft 88 through vertical support member 62. Rotational force is applied from transducer 66b to pulley 76 when the actuator of transducer 66b rotates the shaft. The pulley, in turn, transmits the rotational force to cable 80 and thus forces capstan drum 59 to rotate in a direction about axis B. Extension member 48b rotates with capstan drum 59, thus causing force along the second degree of freedom for object 44. Note that pulley 76, capstan drum 59 and extension member 48b will only actually rotate if the user is not applying the same amount or a greater amount of rotational force to object 44 in the opposite direction to cancel the rotational movement. In any event, the user will feel the rotational force along the second degree of freedom in object 44 as force feedback.

The capstan mechanism 58 provides a mechanical advantage to apparatus 25′ so that the force output of the actuators can be increased. The ratio of the diameter of pulley 76 to the diameter of capstan drum 59 (i.e. double the distance from axis B to the bottom edge 86 of capstan drum 59) dictates the amount of mechanical advantage, similar to a gear system. In the preferred embodiment, the ratio of drum to pulley is equal to 15:1, although other ratios can be used in other embodiments.

Similarly, when the user moves object 44 in the second degree of freedom, extension member 48b rotates about axis B and rotates capstan drum 59 about axis B as well. This movement causes cable 80 to move, which transmits the rotational force to pulley 76. Pulley 76 rotates and causes shaft 88 to rotate, and the direction and magnitude of the movement is detected by the sensor of transducer 66b. A similar process occurs along the first degree of freedom for the other capstan drive mechanism 58. As described above with respect to the actuators, the capstan drive mechanism provides a mechanical advantage to amplify the sensor resolution by a ratio of drum 59 to pulley 76 (15:1 in the preferred embodiment).

Stop 78 is rigidly coupled to vertical support member 62 a few millimeters above curved portion 84 of capstan drum 59. Stop 78 is used to prevent capstan drum 59 from moving beyond a designated angular limit. Thus, drum 59 is constrained to movement within a range defined by the arc length between the ends of leg portion 82. This constrained movement, in turn, constrains the movement of object 44 in the first two degrees of freedom. In the described embodiment, stop 78 is a cylindrical member inserted into a threaded bore in vertical support member 62.

FIG. 5a is a side elevational view of capstan mechanism 58 as shown in FIG. 5. Cable 80 is shown routed along the bottom side 86 of curved portion 84 of capstan drum 59. Cable 80 is preferably wrapped around pulley 76 so that the cable is positioned between threads 90, i.e., the cable is guided by the threads as shown in greater detail in FIG. 5b. As pulley 76 is rotated by transducer 66b or by the manipulations of the user, the portion of cable 80 wrapped around the pulley travels closer to or further from vertical support member 62, depending on the direction that pulley 76 rotates. For example, if pulley 76 is rotated counterclockwise (when viewing the pulley as in FIG. 5), then cable 80 moves toward vertical support member 62 as shown by arrow 92. Capstan drum 59 also rotates clockwise as shown by arrow 94. The threads of pulley 76 are used mainly to provide cable 80 with a better grip on pulley 76. In alternate embodiments, pulley 76 includes no threads, and the high tension in cable 80 allows cable 80 to grip pulley 76.

Capstan drive mechanism 58 is advantageously used in the present invention to provide transmission of forces and mechanical advantage between transducers 66a and 66b and object 44 without introducing substantial compliance, friction, or backlash to the system. A capstan drive provides increased stiffness, so that forces are transmitted with negligible stretch and compression of the components. The amount of friction is also reduced with a capstan drive mechanism so that substantially "noiseless" tactile signals can be provided to the user. In addition, the amount of backlash contributed by a capstan drive is also negligible. "Backlash" is the amount of play that occurs between two coupled rotating objects in a gear or pulley system. Two gears, belts, or other types of drive mechanisms could also be used in place of capstan drive mechanism 58 in alternate embodiments to transmit forces between transducer 66a and extension member 48b. However, gears and the like typically introduce some backlash in the system. In addition, a user might be able to feel the interlocking and grinding of gear teeth during rotation of gears when manipulating object 44; the rotation in a capstan drive mechanism is much less noticeable.

Figure 6:
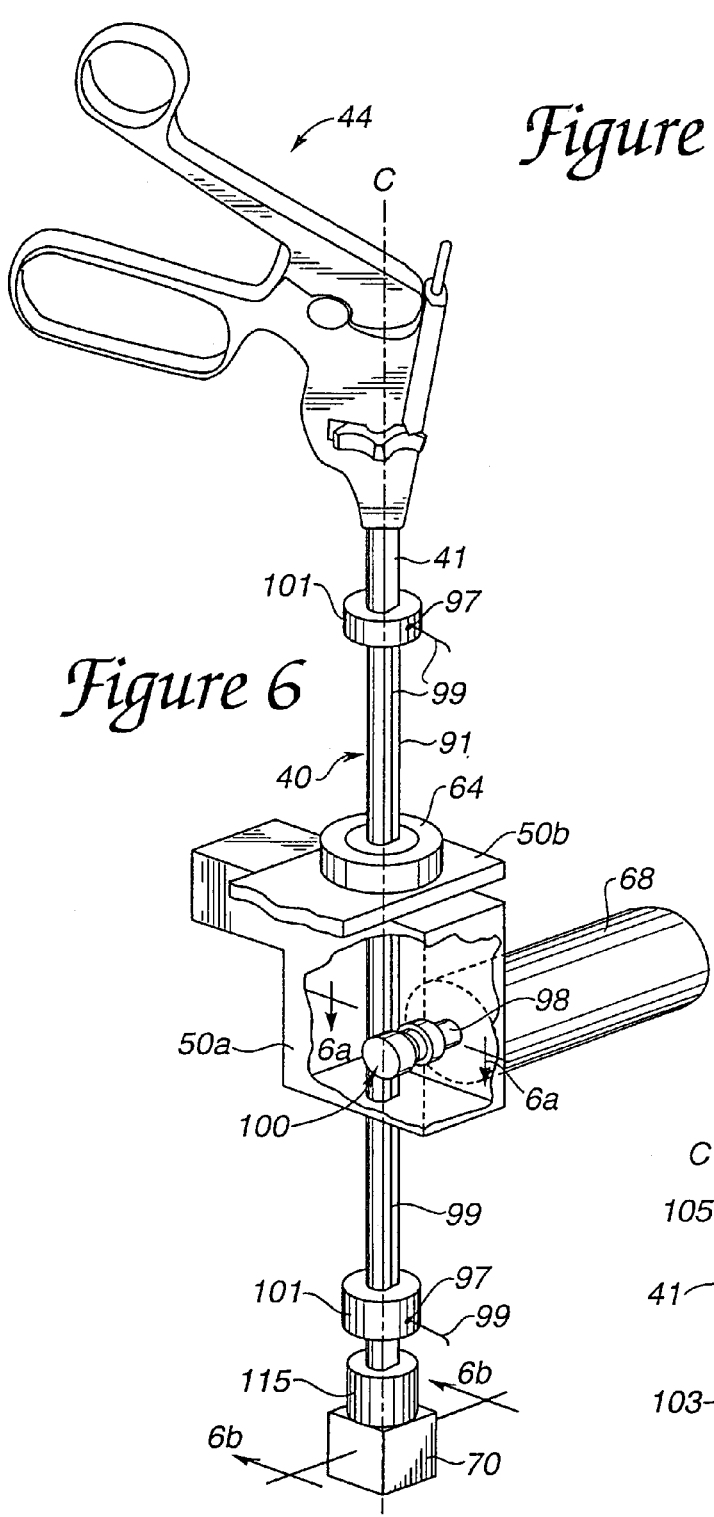
FIG. 6 is a perspective view of a center capstan drive mechanism for a linear axis member of the mechanical apparatus shown in FIG. 3.

FIG. 6 is a perspective view of central drive member 50a and linear axis member 40 shown in some detail. Central drive member 50a is shown in a partial cutaway view to expose the interior of member 50a. Central transducer 68 is coupled to one side of central drive member 50a. In the described embodiment, a capstan drive mechanism is used to transmit forces between transducer 68 and linear axis member 40 along the third degree of freedom. A rotatable shaft 98 of transducer 68 extends through a bore in the side wall of central drive member 50a and is coupled to a capstan pulley 100. Pulley 100 is described in greater detail below with respect to FIG. 6a.

Linear axis member 40 preferably includes an exterior sleeve 91 and an interior shaft 93 (described with reference to FIG. 6b, below). Exterior sleeve 91 is preferably a partially cylindrical member having a flat 41 provided along its length. Flat 41 prevents sleeve 91 from rotating about axis C in the fourth degree of freedom described above. Linear axis member 40 is provided with a cable 99 which is secured on each end of member 40 by tension caps 101. Cable 99 preferably runs down a majority of the length of exterior sleeve 91 on the surface of flat 41 and can be tightened, for example, by releasing a screw 97, pulling an end of cable 99 until the desired tension is achieved, and tightening screw 97. Similarly to the cable of the capstan mechanism described with reference to FIG. 5, cable 99 should have a relatively high tension.

Figure 6B:
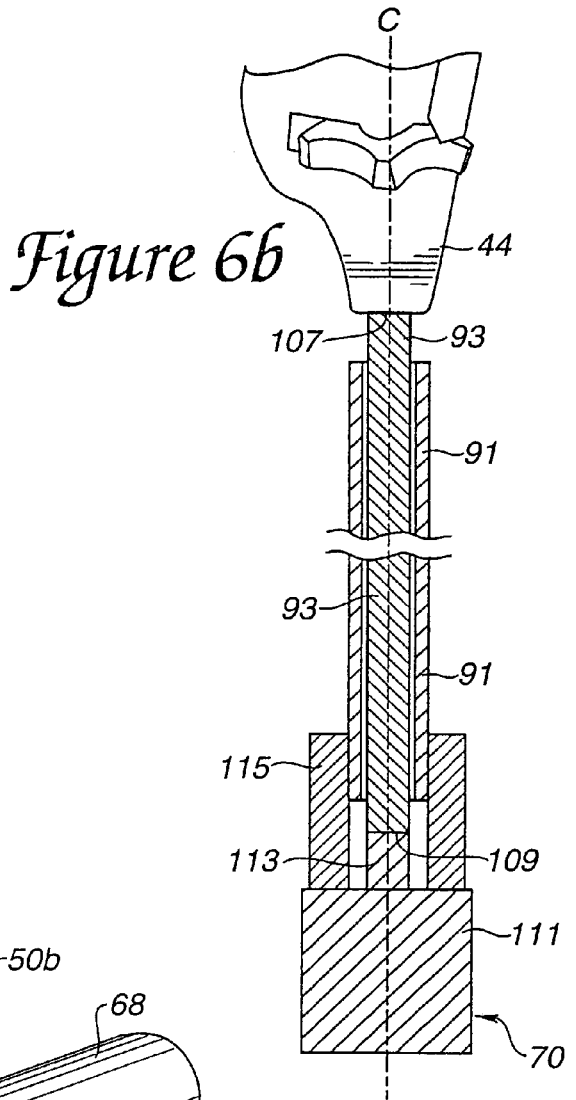
FIG. 6b is a cross sectional side view of the linear axis member and transducer shown in FIG. 6.
Figure 6A:
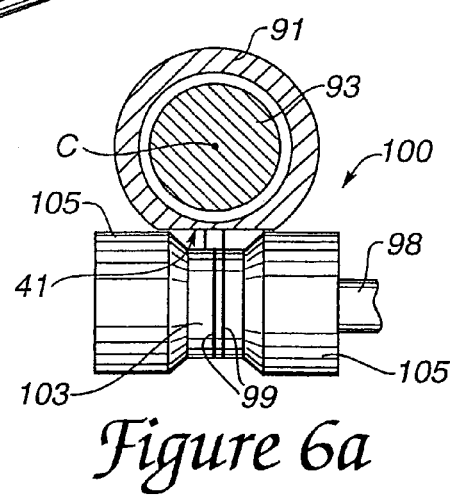
FIG. 6a is a cross sectional top view of a pulley and linear axis member used in the capstan drive mechanism of FIG. 6.

As shown in FIG. 6a, cable 99 is wrapped a number of times around pulley 100 so that forces can be transmitted between pulley 100 and linear axis member 40. Pulley 100 preferably includes a central axle portion 103 and end lip portions 105. Exterior sleeve 91 is preferably positioned such that flat 41 of the sleeve is touching or is very close to lip portions 105 on both sides of axle portion 103. The cable 99 portion around pulley 100 is wrapped around central axle portion 103 and moves along portion 103 towards and away from shaft 98 as the pulley is rotated clockwise and counterclockwise, respectively. The diameter of axle portion 103 is smaller than lip portion 105, providing space between the pulley 100 and flat 41 where cable 99 is attached and allowing free movement of the cable. Pulley 100 preferably does not include threads, unlike pulley 76, since the tension in cable 99 allows the cable to grip pulley 100 tightly. In other embodiments, pulley 100 can be a threaded or unthreaded cylinder similar to capstan pulley 76 described with reference to FIG. 5.

Using the capstan drive mechanism, transducer 68 can translate linear axis member 40 along axis C when the pulley is rotated by the actuator of transducer 68. Likewise, when linear axis member 40 is translated along axis C by the user manipulating object 44, pulley 100 and shaft 98 are rotated; this rotation is detected by the sensor of transducer 68. The capstan drive mechanism provides low friction and smooth, rigid operation for precise movement of linear axis member 40 and accurate position measurement of the member 40.

Other drive mechanisms can also be used to transmit forces to linear axis member and receive positional information from member 40 along axis C. For example, a drive wheel made of a rubber-like material or other frictional material can be positioned on shaft 98 to contact linear axis member 40 along the edge of the wheel. The wheel can cause forces along member 40 from the friction between wheel and linear axis member. Such a drive wheel mechanism is disclosed in the abovementioned application Ser. No. 08/275,120 now U.S. Pat. No. 5,623,582 as well as in U.S. patent application Ser. No. 08/344,148, filed Nov. 23, 1994 and entitled "Method and Apparatus for Providing Mechanical I/O for Computer Systems Interfaced with Elongated Flexible Objects" assigned to the assignee of the present invention and incorporated herein by reference in its entirety. Linear axis member 40 can also be a single shaft in alternate embodiments instead of a dual part sleeve and shaft.

Referring to the cross sectional side view of member 40 and transducer 70 shown in FIG. 6b, interior shaft 93 is positioned inside hollow exterior sleeve 91 and is rotatably coupled to sleeve 91. A first end 107 of shaft 93 preferably extends beyond sleeve 91 and is coupled to object 44. When object 44 is rotated about axis C, shaft 93 is also rotated about axis C in the fourth degree of freedom within sleeve 91. Shaft 93 is translated along axis C in the third degree of freedom when sleeve 91 is translated. Alternatively, interior shaft 93 can be coupled to a shaft of object 44 within exterior sleeve 91. For example, a short portion of shaft 28 of laparoscopic tool 18, as shown in FIG. 1, can extend into sleeve 91 and be coupled to shaft 93 within the sleeve, or shaft 28 can extend all the way to transducer 70 and functionally be used as shaft 93.

Shaft 93 is coupled at its second end 109 to transducer 70, which, in the preferred embodiment, is an optical encoder sensor. The housing 111 of transducer 70 is rigidly coupled to exterior sleeve 91 by a cap 115, and a shaft 113 of transducer 70 is coupled to interior shaft 93 so that transducer 70 can measure the rotational position of shaft 93 and object 44. In alternate embodiments, an actuator can also be included in transducer 70 to provide rotational forces about axle C to shaft 93.

Figure 7:
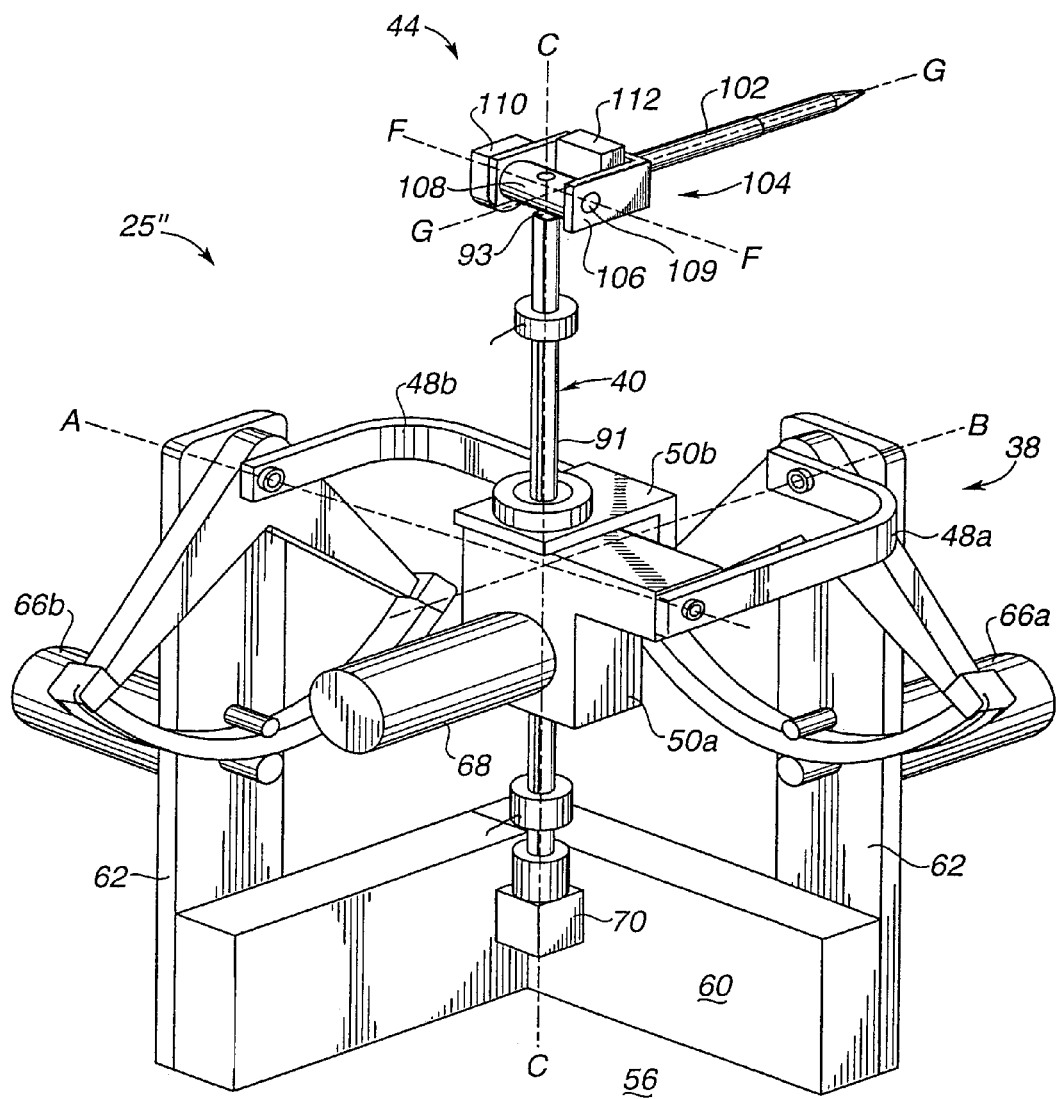
FIG. 7 is a perspective view of an embodiment of the apparatus of FIG. 2 having a stylus object for the user.

FIG. 7 is a perspective view of an alternate embodiment of the mechanical apparatus 25" and user object 44 of the present invention. Mechanical apparatus 25" shown in FIG. 7 operates substantially the same as apparatus 25' shown in FIGS. 3 and 4. User object 44, however, is a stylus 102 which the user can grasp and move in six degrees of freedom. By "grasp", it is meant that users may releasably engage a grip portion of the object in some fashion, such as by hand, with their fingertips, or even orally in the case of handicapped persons. Stylus 102 can be sensed and force can be applied in various degrees of freedom by a computer system and interface such as computer 16 and interface 14 of FIG. 1. Stylus 102 can be used in virtual reality simulations in which the user can move the stylus in 3D space to point to objects, write words, drawings, or other images, etc. For example, a user can view a virtual environment generated on a computer screen or in 3D goggles. A virtual stylus can be presented in a virtual hand of the user. The computer system tracks the position of the stylus with sensors as the user moves it. The computer system also provides force feedback to the stylus when the user moves the stylus against a virtual desk top, writes on a virtual pad of paper, etc. It thus appears and feels to the user that the stylus is contacting a real surface.

Stylus 102 preferably is coupled to a floating gimbal mechanism 104 which provides two degrees of freedom in addition to the four degrees of freedom provided by apparatus 25' described with reference to FIGS. 3 and 4. Floating gimbal mechanism 104 includes a U-shaped member 106 which is rotatably coupled to an axis member 108 by a shaft 109 so that U-shaped member 106 can rotate about axis F. Axis member 108 is rigidly coupled to linear axis member 40. In addition, the housing of a transducer 110 is coupled to U-shaped member 106 and a shaft of transducer 110 is coupled to shaft 109. Shaft 109 is preferably locked into position within axis member 108 so that as U-shaped member 106 is rotated, shaft 109 does not rotate. Transducer 110 is preferably a sensor, such as an optical encoder as described above with reference to transducer 70, which measures the rotation of U-shaped member 106 about axis F in a fifth degree of freedom and provides electrical signals indicating such movement to interface 14.

Stylus 102 is preferably rotatably coupled to U-shaped member 106 by a shaft (not shown) extending through the U-shaped member. This shaft is coupled to a shaft of transducer 112, the housing of which is coupled to U-shaped member 106 as shown. Transducer 112 is preferably a sensor, such as an optical encoder as described above, which measures the rotation of stylus 102 about the lengthwise axis G of the stylus in a sixth degree of freedom.

In the described embodiment of FIG. 7, six degrees of freedom of stylus 102 are sensed. Thus, both the position (x, y, z coordinates) and the orientation (roll, pitch, yaw) of the stylus can be detected by computer 16 to provide a highly realistic simulation. Other mechanisms besides the floating gimbal mechanism 104 can be used to provide the fifth and sixth degrees of freedom. In addition, forces can be applied in three degrees of freedom for stylus 102 to provide 3D force feedback. In alternate embodiments, actuators can also be included in transducers 70, 110, and 112. However, actuators are preferably not included for the fourth, fifth, and sixth degrees of freedom in the described embodiment, since actuators are typically heavier than sensors and, when positioned at the locations of transducers 70, 100, and 112, would create more inertia in the system. In addition, the force feedback for the designated three degrees of freedom allows impacts and resistance to be simulated, which is typically adequate in many virtual reality applications. Force feedback in the fourth, fifth, and sixth degrees of freedom would allow torques on stylus 102 to be simulated as well, which may or may not be useful in a simulation.

Figure 8:
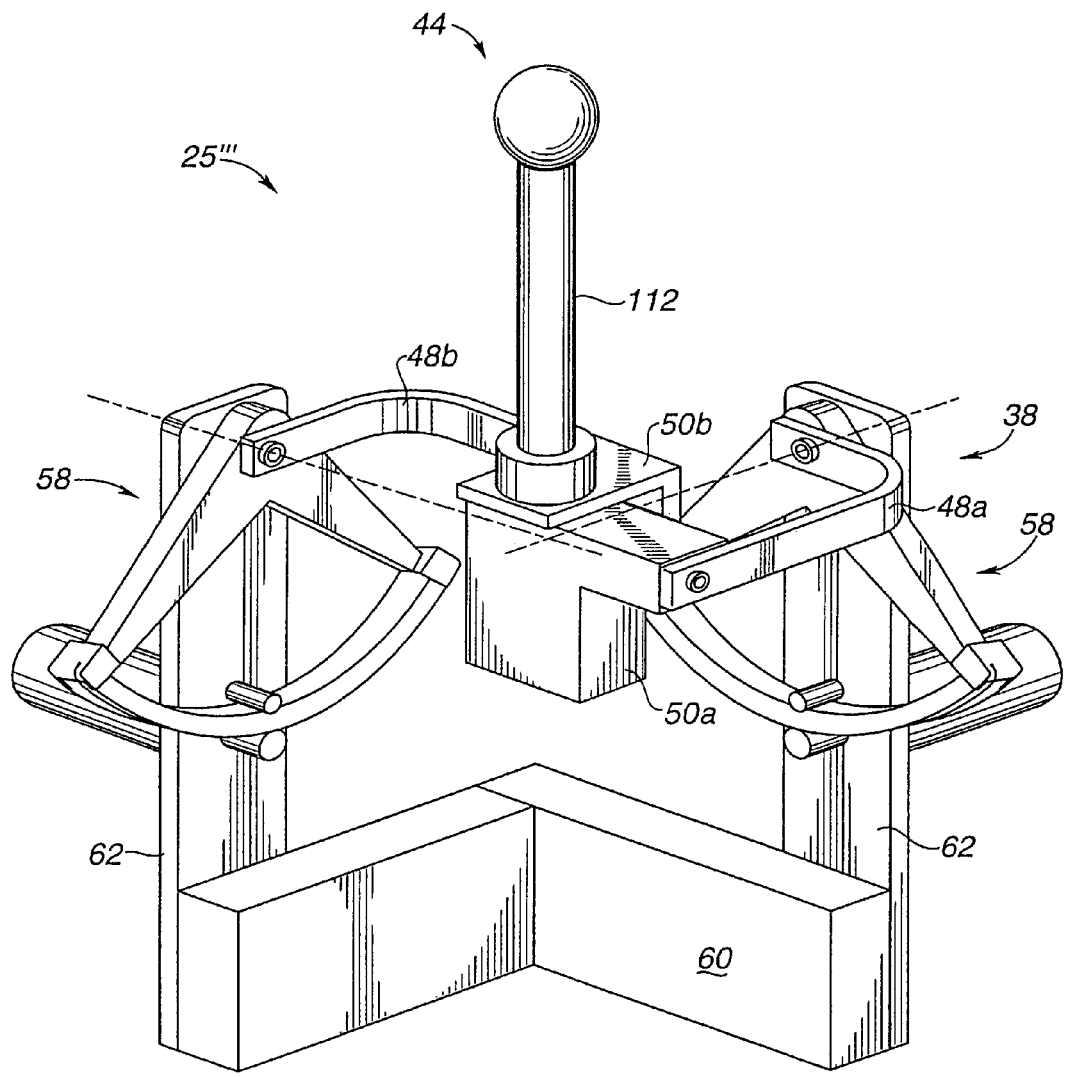
FIG. 8 is a perspective view of an embodiment of the apparatus of FIG. 2 having a joystick object for the user.

FIG. 8 is a perspective view of a second alternate embodiment of the mechanical apparatus 25''' and user object 44 of the present invention. Mechanical apparatus 25''' shown in FIG. 8 operates substantially the same as apparatus 25' shown in FIGS. 3 and 4. User object 44, however, is a joystick 112 which the user can preferably move in two degrees of freedom. Joystick 112 can be sensed and force can be applied in both degrees of freedom by a computer system and interface similar to computer system 16 and interface 14 of FIG. 1. In the described embodiment, joystick 112 is coupled to cylindrical fastener 64 so that the user can move the joystick in the two degrees of freedom provided by gimbal mechanism 38 as described above. Linear axis member 40 is not typically included in the embodiment of FIG. 8, since a joystick is not usually translated along an axis C. However, in alternate embodiments, joystick 112 can be coupled to linear axis member 40 similarly to stylus 102 as shown in FIG. 7 to provide a third degree of freedom. In yet other embodiments, linear axis member 40 can rotate about axis C and transducer 70 can be coupled to apparatus 25''' to provide a fourth degree of freedom. Finally, in other embodiments, a floating gimbal mechanism as shown in FIG. 7, or a different mechanism, can be added to the joystick to allow a full six degrees of freedom.

Joystick 112 can be used in virtual reality simulations in which the user can move the joystick to move a vehicle, point to objects, control a mechanism, etc. For example, a user can view a virtual environment generated on a computer screen or in 3D goggles in which joystick 112 controls an aircraft. The computer system tracks the position of the joystick as the user moves it around with sensors and updates the virtual reality display accordingly to make the aircraft move in the indicated direction, etc. The computer system also provides force feedback to the joystick, for example, when the aircraft is banking or accelerating in a turn or in other situations where the user may experience forces on the joystick or find it more difficult to steer the aircraft.

Figure 9:
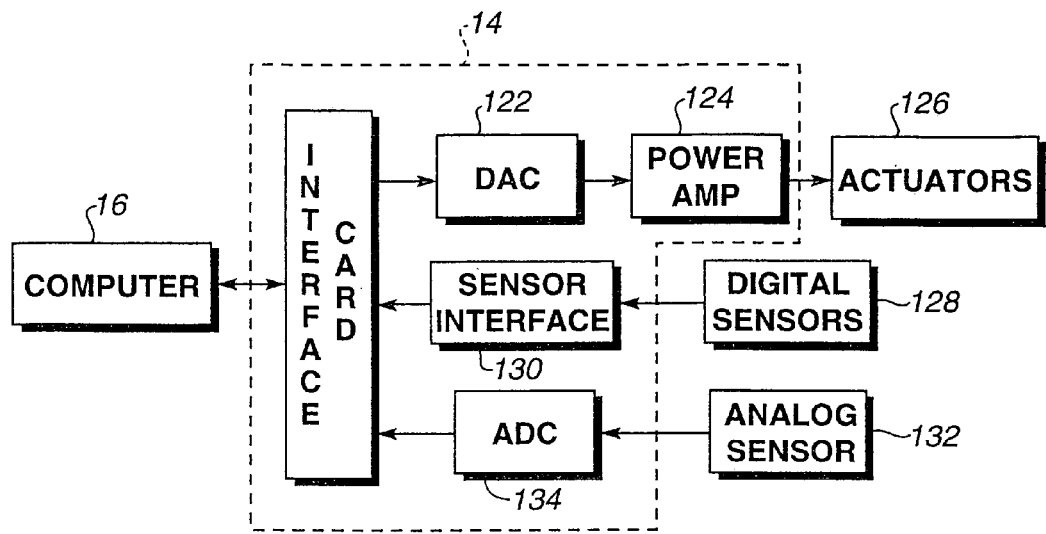
FIG. 9 is a block diagram of a computer and the interface between the computer and the mechanical apparatus of FIG. 2.

FIG. 9 is a schematic view of a computer 16 and an interface circuit 120 used in interface 14 to send and receive signals from mechanical apparatus 25. Circuit 120 includes computer 16, interface card 120, DAC 122, power amplifier circuit 124, digital sensors 128, and sensor interface 130. Optionally included are analog sensors 132 instead of or in addition to digital sensors 128, and ADC 134. In this embodiment, the interface 14 between computer 16 and mechanical apparatus 25 as shown in FIG. 1 can be considered functionally equivalent to the interface circuits enclosed within the dashed line in FIG. 14. Other types of interfaces 14 can also be used. For example, an electronic interface 14 is described in U.S. patent application Ser. No. 08/092,974, filed Jul. 16, 1993 and entitled "3-D Mechanical Mouse" assigned to the assignee of the present invention, which is the parent of file wrapper continuation application Ser. No. 08/461,170, now U.S. Pat. No. 5,576,727, and incorporated herein by reference in its entirety. The electronic interface described therein was designed for the Immersion PROBE™ 3-D mechanical mouse and has six channels corresponding to the six degrees of freedom of the Immersion PROBE.

Interface card 120 is preferably a card which can fit into an interface slot of computer 16. For example, if computer 16 is an IBM AT compatible computer, interface card 14 can be implemented as an ISA or other well-known standard interface card which plugs into the motherboard of the computer and provides input and output ports connected to the main data bus of the computer.

Digital to analog converter (DAC) 122 is coupled to interface card 120 and receives a digital signal from computer 16. DAC 122 converts the digital signal to analog voltages which are then sent to power amplifier circuit 124. A DAC circuit suitable for use with the present invention is described with reference to FIG. 10. Power amplifier circuit 124 receives an analog low-power control voltage from DAC 122 and amplifies the voltage to control actuators 126. Power amplifier circuit 124 is described in greater detail with reference to FIG. 11. Actuators 126 are preferably DC servo motors incorporated into the transducers 66a, 66b, and 68, and any additional actuators, as described with reference to the embodiments shown in FIGS. 3, 7, and 8 for providing force feedback to a user manipulating object 44 coupled to mechanical apparatus 25.

Digital sensors 128 provide signals to computer 16 relating the position of the user object 44 in 3D space. In the preferred embodiments described above, sensors 128 are relative optical encoders, which are electro-optical devices that respond to a shaft's rotation by producing two phase-related signals. In the described embodiment, sensor interface circuit 130, which is preferably a single chip, receives the signals from digital sensors 128 and converts the two signals from each sensor into another pair of clock signals, which drive a bi-directional binary counter. The output of the binary counter is received by computer 16 as a binary number representing the angular position of the encoded shaft. Such circuits, or equivalent circuits, are well known to those skilled in the art; for example, the Quadrature Chip from Hewlett Packard, California performs the functions described above.

Analog sensor 132 can be included instead of digital sensors 128 for all or some of the transducers of the present invention. For example, a strain gauge can be connected to stylus 130 of FIG. 7 to measure forces. Analog sensors 132 provide an analog signal representative of the position of the user object in a particular degree of motion. Analog to digital converter (ADC) 134 converts the analog signal to a digital signal that is received and interpreted by computer 16, as is well known to those skilled in the art.

Figure 10:
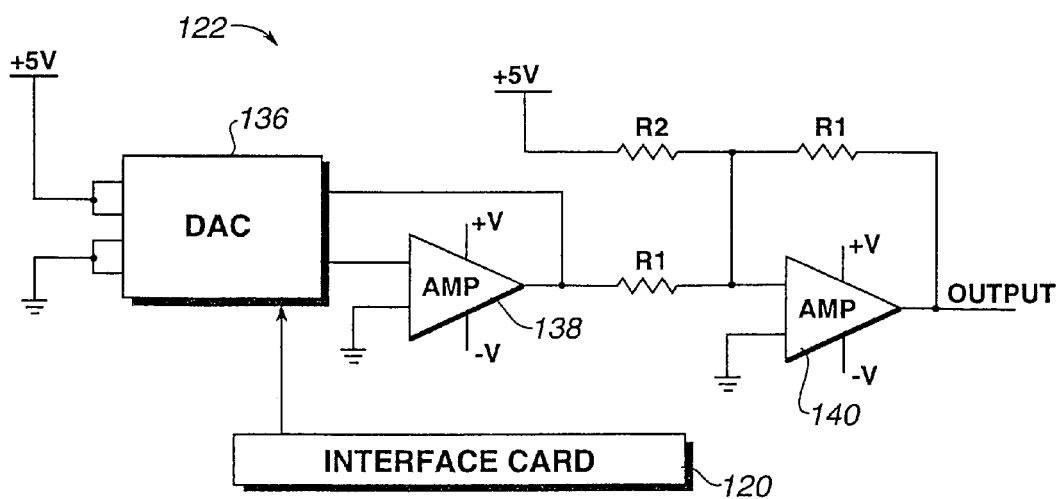
FIG. 10 is a schematic diagram of a suitable circuit for a digital to analog controller of the interface of FIG. 9.

FIG. 10 is a schematic view of a DAC circuit 122 of FIG. 9 suitable for converting an input digital signal to an analog voltage that is output to power amplifier circuit 124. In the described embodiment, circuit 122 includes a parallel DAC 136, such as the DAC1220 manufactured by National Semiconductor, which is designed to operate with an external generic op amp 138. Op amp 138, for example, outputs a signal from zero to −5 volts proportional to the binary number at its input. Op amp 140 is an inverting summing amplifier that converts the output voltage to a symmetrical bipolar range. Op amp 140 produces an output signal between −2.5 V and +2.5 V by inverting the output of op amp 138 and subtracting 2.5 volts from that output; this output signal is suitable for power amplification in amplification circuit 124. As an example, R1=200 kΩ and R2=400 kΩ. Of course, circuit 122 is intended as one example of many possible circuits that can be used to convert a digital signal to a desired analog signal.

Figure 11:
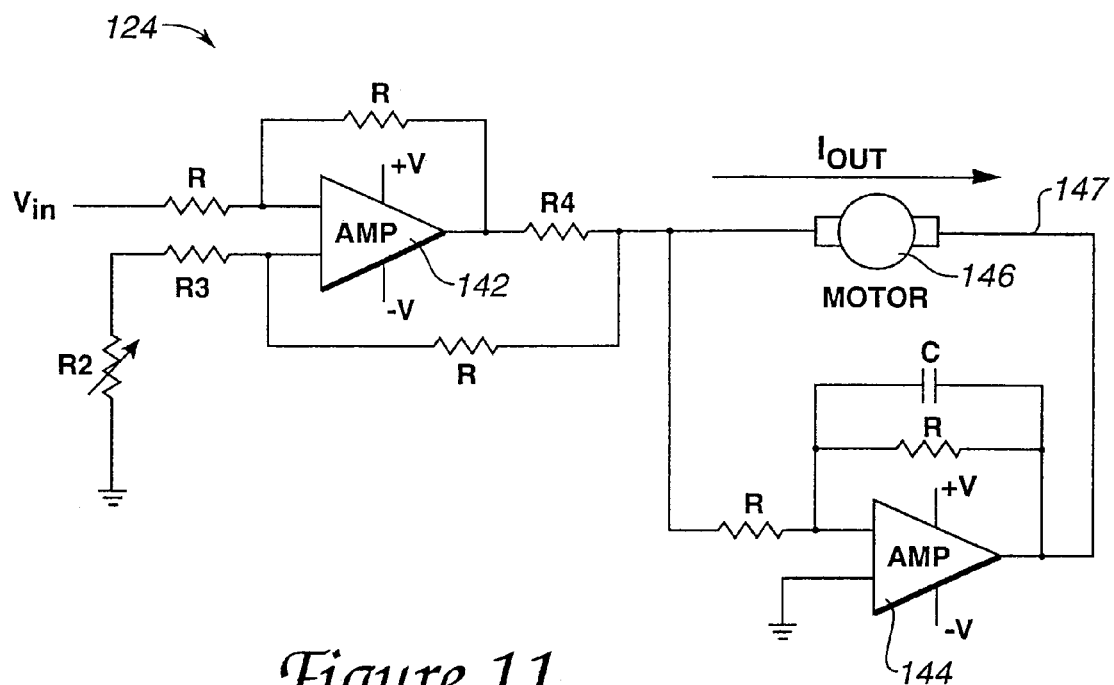
FIG. 11 is a schematic diagram of a suitable power amplification circuit for powering the actuators of the present invention as shown in FIG. 9.

FIG. 11 is a schematic view of a power amplifier circuit 124 suitable for use in the interface circuit 14 shown in FIG. 9. Power amplifier circuit receives a low power control voltage from DAC circuit 122 to control high-power, current-controlled servo motor 126. The input control voltage controls a transconductance stage composed of amplifier 142 and several resistors. The transconductance stage produces an output current proportional to the input voltage to drive motor 126 while drawing very little current from the input voltage source. The second amplifier stage, including amplifier 144, resistors, and a capacitor C, provides additional current capacity by enhancing the voltage swing of the second terminal 147 of motor 146. As example values for circuit 124, R=10 kΩ, R2=500 Ω, R3=9.75 kΩ, and R4=1 Ω. Of course, circuit 124 is intended as one example of many possible circuits that can be used to amplify voltages to drive actuators 126.

While this invention has been described in terms of several preferred embodiments, it is contemplated that alterations, modifications and permutations thereof will become apparent to those skilled in the art upon a reading of the specification and study of the drawings. For example, the linked members of apparatus 25 can take a number of actual physical sizes and forms while maintaining the disclosed linkage structure. In addition, other gimbal mechanisms can also be provided with a linear axis member 40 to provide three degrees of freedom. Likewise, other types of gimbal mechanisms or different mechanisms providing multiple degrees of freedom can be used with the capstan drive mechanisms disclosed herein to reduce inertia, friction, and backlash in a system. A variety of devices can also be used to sense the position of an object in the provided degrees of freedom and to drive the object along those degrees of freedom. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. An apparatus, comprising:
   a user object including an elongated portion;
   a closed-loop five member linkage coupled to the user object and configured to enable the user object to move in a first rotary degree of freedom, a second rotary degree of freedom, and in a translational degree of freedom, the close-loop five member linkage including a serial-linked chain of a ground member, a first extension member, a first central member, a second central member and a second extension member, the first and second central members being coupled to the user object respectively via a first object coupling and a second object coupling such that the first and second central members are substantially non-parallel with respect to the elongated portion of the user object, the first central member being fixedly coupled to the first object coupling, the second central member being fixedly coupled to the second object coupling; and
   at least one sensor coupled to the closed-loop five member linkage and operative to detect a movement of the user object in at least one degree of freedom.

2. An apparatus according to claim 1, wherein the user object includes a grip portion and an elongated portion.

3. An apparatus according to claim 2, wherein the grip portion further includes a first member and a second member, the first and second members movable relative to one another to simulate a cutting blade of a medical instrument.

4. An apparatus according to claim 3, further comprising a transducer coupled to the grip portion of the user object, the transducer responsive to a relative motion of the first and second members.

5. An apparatus according to claim 2, wherein the grip portion includes a finger wheel.

6. An apparatus according to claim 2, further comprising a barrier disposed between the grip portion and the closed-loop five member linkage.

7. An apparatus according to claim 2, further comprising a trocar disposed between the grip portion and the closed-loop five member linkage.

8. An apparatus according to claim 1, wherein the use object is representative of one of a laparoscopic instrument, an endoscopic instrument, a catheter, a hypodermic needle, a fiber optic bundle, a joystick, a screw driver, and a pool cue.

9. An apparatus according to claim 1, wherein the detection of the at least one sensor associated with the movement of the user object is input to a virtual reality simulation.

10. An apparatus according to claim 9, wherein the virtual reality simulation includes a medical procedure.

11. An apparatus according to claim 9, wherein the feedback force is correlated with the virtual reality simulation.

12. An apparatus according to claim 1, further comprising at least one capstan drive mechanism coupled to the at least one actuator and to the closed-loop five member linkage, the at least one capstan mechanism configured to facilitate a transmission of the feedback force from the at least one actuator to the closed-loop five member linkage.

13. An apparatus according to claim 12, wherein the at least one capstan mechanism includes an assembly of a capstan drum, a one cable, and a pulley.

14. An apparatus according to claim 1, wherein the at least one actuator includes a motor.

15. An apparatus according to claim 1, wherein the at least one actuator includes a braking mechanism.

16. An apparatus, comprising:
    a user object including a grip portion and an elongated portion, the user object being configured to represent a laparoscopic surgical instrument;
    a closed-loop five member linkage coupled to the user object and configured to enable the user object to move in a first rotary degree of freedom, a second rotary degree of freedom, and in a translational degree of freedom, the close-loop five member linkage including a serial-linked chain of a ground member, a first extension member, a first central member, a second central member and a second extension member, the first and second central members being coupled to the user object respectively via a first object coupling and a second object coupling such that the first and second central members are substantially non-parallel with respect to the elongated portion of the user object, the first central member being fixedly coupled to the first object coupling, the second central member being fixedly coupled to the second object coupling;
    at least one sensor coupled to the closed-loop five member linkage and operative to detect a movement of the user object in at least one degree of freedom, the detection of the at least one sensor associated with the movement of the user object being input to a laparoscopic surgical simulation; and
    at least one actuator coupled to the closed-loop five member linkage and configured to output a feedback force, the feedback force being correlated with the laparoscopic surgical simulation.

17. An apparatus according to claim 16, further comprising at least one capstan mechanism coupled to the at least one actuator and the closed-loop five member linkage.

18. An apparatus according to claim 16, wherein the at least one actuator includes a plurality of actuators, each actuator being associated with one of the first and second rotational degrees of freedom and the translational degree of freedom.

19. An apparatus according to claim 16, wherein the grip portion further includes a first member and a second member movable relative to one another, configured to simulate a cutting blade in the laparoscopic surgical instrument.

20. An apparatus according to claim 19, further comprising a transducer coupled to the grip portion, the transducer responsive to a relative motion of the first and second members.

21. An apparatus according to claim 16, further comprising a barrier disposed between the grip portion and the closed-loop five member linkage.

22. An apparatus according to claim 16, further comprising a trocar disposed between the grip portion and the closed-loop five member linkage.

23. An apparatus according to claim 16, wherein the at least one actuator includes one of a motor and a braking mechanism.

* * * * *